United States Patent
Ly et al.

(10) Patent No.: US 9,500,188 B2
(45) Date of Patent: Nov. 22, 2016

(54) MEDICAL FLUID CASSETTES AND RELATED SYSTEMS AND METHODS

(75) Inventors: Tri Ly, Dublin, CA (US); Gurpreet Singh, Antioch, CA (US); Michael David Young, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 449 days.

(21) Appl. No.: 13/493,598

(22) Filed: Jun. 11, 2012

(65) Prior Publication Data

US 2013/0330208 A1    Dec. 12, 2013

(51) Int. Cl.
F04B 17/04    (2006.01)
F04B 43/04    (2006.01)

(52) U.S. Cl.
CPC .............. *F04B 17/042* (2013.01); *F04B 43/04* (2013.01); *A61M 2205/12* (2013.01)

(58) Field of Classification Search
CPC ..................... A61M 5/14224; A61M 2205/12; A61M 1/28; A61M 2205/121; A61M 2205/122; A61M 2205/125; A61M 2205/126; A61M 2205/127; A61M 2205/14212; F04B 17/04; F04B 17/042; F04B 17/044; F04B 43/04; F04B 35/045; F04B 45/047
USPC ......... 417/415, 413.1, 360, 417, 442, 477.2; 604/151, 152, 153; 92/99, 101
See application file for complete search history.

(56) References Cited

U.S. PATENT DOCUMENTS

| | | | |
|---|---|---|---|
| 329,773 A | 11/1885 | Perry | |
| 2,383,193 A | 8/1945 | Herbert | |
| 2,529,028 A | 11/1950 | Landon | |
| 2,658,526 A | 11/1953 | Porter | |
| 2,711,134 A | 6/1955 | Hughes | |
| 2,755,745 A | 7/1956 | Lewis | |
| 2,871,795 A | 2/1959 | Smith | |
| 2,886,281 A | 5/1959 | Canalizo | |
| 3,083,943 A | 4/1963 | Stewart, Jr. et al. | |
| 3,323,786 A | 6/1967 | Boschi | |
| 3,556,465 A | 1/1971 | Little | |
| 3,671,814 A * | 6/1972 | Heinrich | 361/154 |
| 3,689,025 A | 9/1972 | Kiser et al. | |
| 3,741,687 A | 6/1973 | Nystroem | |

(Continued)

FOREIGN PATENT DOCUMENTS

| | | |
|---|---|---|
| DE | 2628238 | 1/1978 |
| DE | 2827648 | 1/1979 |

(Continued)

OTHER PUBLICATIONS

U.S. Appl. No. 13/493,598—Google definition for Hall Effect Sensor, accessed Jul. 30, 2015.*

(Continued)

*Primary Examiner* — Devon Kramer
*Assistant Examiner* — Jon Hoffmann
(74) *Attorney, Agent, or Firm* — Fish & Richardson P.C.

(57) ABSTRACT

This disclosure relates to medical fluid cassettes and related systems and methods. In some aspects, a medical fluid cassette includes a base and a magnetically attractive member overlying a fluid pump chamber of the cassette. The magnetically attractive member defines a cavity sized and shaped to receive a portion of a piston.

22 Claims, 13 Drawing Sheets

(56) References Cited

U.S. PATENT DOCUMENTS

| | | | |
|---|---|---|---|
| 3,777,625 A * | 12/1973 | Andres | F15B 15/10 |
| | | | 92/48 |
| 3,781,141 A * | 12/1973 | Schall | F01L 25/063 |
| | | | 417/395 |
| 3,880,053 A * | 4/1975 | Trechsel | F04B 15/00 |
| | | | 92/103 R |
| 3,927,955 A | 12/1975 | Spinosa et al. | |
| 3,966,358 A | 6/1976 | Heimes et al. | |
| 3,985,135 A | 10/1976 | Carpenter et al. | |
| 4,026,669 A | 5/1977 | Leonard et al. | |
| 4,047,844 A | 9/1977 | Robinson | |
| 4,050,859 A * | 9/1977 | Vork | F04B 53/1032 |
| | | | 417/386 |
| 4,091,812 A | 5/1978 | Helixon et al. | |
| 4,121,584 A | 10/1978 | Turner et al. | |
| 4,152,098 A | 5/1979 | Moody et al. | |
| 4,158,530 A | 6/1979 | Bernstein | |
| 4,178,940 A | 12/1979 | Au | |
| 4,273,121 A | 6/1981 | Jassawalla | |
| 4,303,376 A | 12/1981 | Siekmann | |
| 4,304,260 A | 12/1981 | Turner et al. | |
| 4,322,201 A | 3/1982 | Archibald | |
| 4,333,452 A | 6/1982 | Au | |
| 4,370,983 A | 2/1983 | Lichtenstein | |
| 4,382,753 A | 5/1983 | Archibald | |
| 4,410,322 A | 10/1983 | Archibald | |
| 4,412,553 A | 11/1983 | Kopp et al. | |
| 4,436,620 A | 3/1984 | Bellotti et al. | |
| 4,453,932 A | 6/1984 | Pastrone | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,490,621 A | 12/1984 | Watabe et al. | |
| 4,536,201 A | 8/1985 | Brorsson et al. | |
| 4,558,715 A | 12/1985 | Walton et al. | |
| 4,569,378 A | 2/1986 | Bergandy | |
| 4,583,920 A | 4/1986 | Lindner | |
| 4,597,412 A | 7/1986 | Stark | |
| 4,610,605 A * | 9/1986 | Hartley | F04B 43/0054 |
| | | | 417/269 |
| 4,623,328 A | 11/1986 | Hartranft | |
| 4,628,499 A | 12/1986 | Hammett | |
| 4,639,245 A | 1/1987 | Pastrone et al. | |
| 4,643,713 A | 2/1987 | Viitala | |
| 4,657,490 A | 4/1987 | Abbott | |
| 4,662,598 A | 5/1987 | Weingarten | |
| 4,662,906 A | 5/1987 | Matkovich et al. | |
| 4,676,467 A | 6/1987 | Palsulich | |
| 4,690,621 A | 9/1987 | Swain | |
| 4,703,913 A | 11/1987 | Hunkapiller | |
| 4,705,259 A | 11/1987 | Dolhen et al. | |
| 4,710,166 A | 12/1987 | Thompson et al. | |
| 4,735,558 A | 4/1988 | Kienholz et al. | |
| 4,778,451 A | 10/1988 | Kamen | |
| 4,786,240 A * | 11/1988 | Koroly et al. | 417/413.1 |
| 4,808,161 A | 2/1989 | Kamen | |
| 4,826,482 A | 5/1989 | Kamen | |
| 4,840,542 A | 6/1989 | Abbott | |
| 4,842,584 A | 6/1989 | Pastrone | |
| 4,846,636 A | 7/1989 | Danby et al. | |
| 4,850,980 A | 7/1989 | Lentz et al. | |
| 4,858,883 A | 8/1989 | Webster | |
| 4,902,282 A | 2/1990 | Bellotti et al. | |
| 4,906,260 A | 3/1990 | Emheiser et al. | |
| 4,927,411 A | 5/1990 | Pastrone et al. | |
| 4,950,134 A | 8/1990 | Bailey et al. | |
| 4,974,754 A | 12/1990 | Wirz | |
| 4,976,162 A | 12/1990 | Kamen | |
| 4,995,864 A | 2/1991 | Bartholomew et al. | |
| 4,997,464 A | 3/1991 | Kopf | |
| 5,002,471 A * | 3/1991 | Perlov | F04B 43/0054 |
| | | | 417/413.1 |
| 5,006,050 A | 4/1991 | Cooke et al. | |
| 5,011,380 A * | 4/1991 | Kovacs | 417/413.1 |
| 5,036,886 A | 8/1991 | Olsen et al. | |
| 5,061,236 A | 10/1991 | Sutherland et al. | |
| 5,088,515 A | 2/1992 | Kamen | |
| 5,098,262 A | 3/1992 | Wecker et al. | |
| 5,100,380 A | 3/1992 | Epstein et al. | |
| 5,100,699 A | 3/1992 | Roeser | |
| 5,116,021 A | 5/1992 | Faust et al. | |
| 5,116,316 A | 5/1992 | Sertic et al. | |
| 5,146,713 A | 9/1992 | Grafius | |
| 5,151,019 A | 9/1992 | Danby et al. | |
| 5,167,837 A | 12/1992 | Snodgrass et al. | |
| 5,171,029 A | 12/1992 | Maxwell et al. | |
| 5,178,182 A | 1/1993 | Kamen | |
| 5,193,990 A | 3/1993 | Kamen et al. | |
| 5,211,201 A | 5/1993 | Kamen et al. | |
| 5,241,985 A | 9/1993 | Faust et al. | |
| 5,247,434 A | 9/1993 | Peterson et al. | |
| 5,249,932 A | 10/1993 | Van Bork | |
| 5,252,044 A | 10/1993 | Raines et al. | |
| 5,259,352 A | 11/1993 | Gerhardy et al. | |
| 5,267,956 A | 12/1993 | Beuchat | |
| 5,279,556 A | 1/1994 | Goi et al. | |
| 5,302,093 A | 4/1994 | Owens et al. | |
| 5,324,422 A | 6/1994 | Colleran et al. | |
| 5,330,425 A | 7/1994 | Utterberg | |
| 5,342,182 A | 8/1994 | Montoya et al. | |
| 5,344,292 A | 9/1994 | Rabenau et al. | |
| 5,350,357 A | 9/1994 | Kamen et al. | |
| D351,470 S | 10/1994 | Scherer et al. | |
| 5,353,837 A | 10/1994 | Faust | |
| 5,378,126 A | 1/1995 | Abrahamson et al. | |
| 5,395,351 A | 3/1995 | Munsch | |
| 5,413,626 A | 5/1995 | Bartsch | |
| 5,415,528 A | 5/1995 | Ogden et al. | |
| 5,421,208 A | 6/1995 | Packard et al. | |
| 5,421,823 A | 6/1995 | Kamen et al. | |
| 5,427,509 A | 6/1995 | Chapman et al. | |
| 5,431,626 A | 7/1995 | Bryant et al. | |
| 5,431,627 A | 7/1995 | Pastrone et al. | |
| 5,431,634 A | 7/1995 | Brown | |
| 5,438,510 A | 8/1995 | Bryant et al. | |
| 5,441,636 A | 8/1995 | Chevallet et al. | |
| 5,445,506 A | 8/1995 | Afflerbaugh et al. | |
| 5,447,286 A | 9/1995 | Kamen et al. | |
| 5,462,416 A | 10/1995 | Dennehey et al. | |
| 5,462,417 A | 10/1995 | Chapman | |
| 5,474,683 A | 12/1995 | Bryant et al. | |
| 5,478,211 A | 12/1995 | Dominiak et al. | |
| 5,480,294 A | 1/1996 | Di Perna et al. | |
| 5,482,438 A | 1/1996 | Anderson et al. | |
| 5,482,440 A | 1/1996 | Dennehey et al. | |
| 5,482,446 A | 1/1996 | Williamson et al. | |
| 5,484,239 A | 1/1996 | Chapman et al. | |
| 5,486,286 A | 1/1996 | Peterson et al. | |
| 5,514,069 A | 5/1996 | Brown et al. | |
| 5,538,405 A | 7/1996 | Patno et al. | |
| 5,540,568 A | 7/1996 | Rosen et al. | |
| 5,547,453 A | 8/1996 | Di Perna | |
| 5,551,850 A | 9/1996 | Williamson et al. | |
| 5,551,941 A | 9/1996 | Howell | |
| 5,551,942 A | 9/1996 | Brown et al. | |
| 5,554,013 A | 9/1996 | Owens et al. | |
| 5,570,716 A | 11/1996 | Kamen et al. | |
| 5,573,385 A | 11/1996 | Chevallier | |
| 5,578,070 A | 11/1996 | Utterberg | |
| 5,588,816 A | 12/1996 | Abbott et al. | |
| 5,593,290 A | 1/1997 | Greisch et al. | |
| 5,599,174 A * | 2/1997 | Cook et al. | 417/413.1 |
| 5,609,572 A | 3/1997 | Lang | |
| 5,614,677 A | 3/1997 | Wamsiedler et al. | |
| 5,624,409 A * | 4/1997 | Seale | A61M 5/16809 |
| | | | 604/246 |
| 5,628,908 A | 5/1997 | Kamen et al. | |
| 5,630,710 A | 5/1997 | Tune et al. | |
| 5,634,391 A | 6/1997 | Eady | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |

(56) References Cited

U.S. PATENT DOCUMENTS

| | | |
|---|---|---|
| 5,643,205 A | 7/1997 | Utterberg |
| 5,645,531 A | 7/1997 | Thompson et al. |
| 5,658,133 A | 8/1997 | Anderson et al. |
| 5,669,764 A | 9/1997 | Behringer et al. |
| 5,690,602 A | 11/1997 | Brown et al. |
| D390,654 S | 2/1998 | Alsberg et al. |
| 5,713,865 A | 2/1998 | Manning et al. |
| 5,713,888 A | 2/1998 | Neuenfeldt et al. |
| 5,718,567 A | 2/1998 | Rapp et al. |
| 5,741,125 A | 4/1998 | Neftel et al. |
| 5,743,169 A * | 4/1998 | Yamada ............ B29C 45/14467 92/100 |
| 5,746,708 A | 5/1998 | Giesler et al. |
| 5,755,683 A | 5/1998 | Houle et al. |
| 5,764,034 A | 6/1998 | Bowman et al. |
| 5,769,387 A | 6/1998 | Perez |
| 5,771,914 A | 6/1998 | Ling et al. |
| 5,772,635 A | 6/1998 | Dastur et al. |
| 5,772,637 A | 6/1998 | Heinzmann et al. |
| 5,775,371 A | 7/1998 | Pan et al. |
| 5,782,575 A | 7/1998 | Vincent et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,902,096 A | 5/1999 | Behringer et al. |
| 5,906,598 A | 5/1999 | Giesler et al. |
| 5,921,951 A | 7/1999 | Morris |
| 5,925,011 A | 7/1999 | Faict et al. |
| 5,934,885 A | 8/1999 | Farrell et al. |
| 5,935,099 A | 8/1999 | Peterson et al. |
| 5,938,634 A | 8/1999 | Packard |
| 5,984,897 A | 11/1999 | Petersen et al. |
| 5,989,423 A | 11/1999 | Kamen |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,074,359 A | 6/2000 | Keshaviah et al. |
| 6,079,959 A | 6/2000 | Kingsford et al. |
| 6,099,492 A | 8/2000 | Le Boeuf |
| 6,106,246 A | 8/2000 | Steck et al. |
| 6,110,410 A | 8/2000 | Owens et al. |
| 6,118,207 A | 9/2000 | Ormerod et al. |
| 6,129,517 A | 10/2000 | Danby et al. |
| 6,132,187 A | 10/2000 | Ericson |
| 6,136,565 A | 10/2000 | Best et al. |
| 6,152,705 A | 11/2000 | Kennedy et al. |
| 6,154,605 A | 11/2000 | Aonuma |
| 6,164,621 A | 12/2000 | Bouchard et al. |
| 6,165,154 A | 12/2000 | Gray et al. |
| 6,168,394 B1 | 1/2001 | Forman et al. |
| 6,178,996 B1 | 1/2001 | Suzuki |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,196,987 B1 | 3/2001 | Holmes et al. |
| 6,200,287 B1 | 3/2001 | Keller et al. |
| 6,206,644 B1 | 3/2001 | Pereira et al. |
| 6,208,107 B1 | 3/2001 | Maske et al. |
| 6,208,497 B1 * | 3/2001 | Seale et al. ............ 361/160 |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,227,807 B1 | 5/2001 | Chase |
| 6,227,824 B1 | 5/2001 | Stehr |
| 6,228,047 B1 | 5/2001 | Dadson |
| 6,229,753 B1 | 5/2001 | Kono et al. |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,286,566 B1 | 9/2001 | Cline et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,312,412 B1 | 11/2001 | Saied et al. |
| 6,315,707 B1 | 11/2001 | Smith et al. |
| 6,315,754 B1 | 11/2001 | Daoud et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,367,669 B1 | 4/2002 | Au et al. |
| 6,382,923 B1 | 5/2002 | Gray |
| 6,383,158 B1 | 5/2002 | Utterberg |
| 6,402,486 B1 | 6/2002 | Steck et al. |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,484,383 B1 | 11/2002 | Herklotz |
| 6,489,896 B1 | 12/2002 | Platt et al. |
| 6,491,656 B1 | 12/2002 | Morris |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,579,253 B1 | 6/2003 | Burbank et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Lee et al. |
| 6,672,841 B1 | 1/2004 | Herklotz et al. |
| 6,695,593 B1 | 2/2004 | Steck et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Doenig et al. |
| 6,746,514 B2 | 6/2004 | Bedingfield et al. |
| 6,749,403 B2 | 6/2004 | Bryant et al. |
| 6,752,172 B2 | 6/2004 | Lauer |

(56) References Cited

U.S. PATENT DOCUMENTS

| | | |
|---|---|---|
| 6,752,599 B2 | 6/2004 | Park |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,759,014 B2 | 7/2004 | Dales et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,014 B2 | 9/2004 | Bowen |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,957,952 B1 | 10/2005 | Steck et al. |
| 6,984,218 B2 | 1/2006 | Nayak et al. |
| 7,021,148 B2 | 4/2006 | Kuhn et al. |
| 7,029,245 B2 | 4/2006 | Maianti et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman et al. |
| 7,195,607 B2 | 3/2007 | Westberg et al. |
| 7,211,560 B2 | 5/2007 | Looker et |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,261,559 B2 | 8/2007 | Smith et al. |
| 7,267,661 B2 | 9/2007 | Susi |
| 7,273,465 B2 | 9/2007 | Ash |
| 7,306,578 B2 | 12/2007 | Gray et al. |
| 7,331,935 B2 | 2/2008 | Barere |
| 7,338,469 B2 | 3/2008 | Barker et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,461,968 B2 | 12/2008 | Demers et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,133 B2 | 2/2010 | Scarborough et al. |
| 7,662,286 B2 | 2/2010 | Childers et al. |
| 7,699,966 B2 | 4/2010 | Qin et al. |
| 7,717,682 B2 | 5/2010 | Orr |
| 7,789,849 B2 | 9/2010 | Busby et al. |
| 7,815,595 B2 | 10/2010 | Busby et al. |
| 8,038,640 B2 | 10/2011 | Orr |
| 8,197,231 B2 | 6/2012 | Orr |
| 8,197,439 B2 | 6/2012 | Wang et al. |
| 8,206,338 B2 | 6/2012 | Childers et al. |
| 8,292,594 B2 | 10/2012 | Tracey et al. |
| 8,366,921 B2 | 2/2013 | Beden et al. |
| 8,409,441 B2 | 4/2013 | Wilt |
| 8,562,834 B2 | 10/2013 | Kamen et al. |
| 8,721,879 B2 | 5/2014 | van der Merwe et al. |
| 2001/0034502 A1 | 10/2001 | Moberg |
| 2001/0037763 A1 | 11/2001 | Deguchi et al. |
| 2001/0043450 A1* | 11/2001 | Seale et al. ............... 361/160 |
| 2002/0045851 A1 | 4/2002 | Suzuki et al. |
| 2002/0062109 A1 | 5/2002 | Lauer |
| 2002/0072718 A1 | 6/2002 | Brugger et al. |
| 2002/0098097 A1* | 7/2002 | Singh .................. 417/413.1 |
| 2002/0107474 A1 | 8/2002 | Noack |
| 2002/0141529 A1 | 10/2002 | Olsher et al. |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0194332 A1 | 10/2003 | Jahn et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0001766 A1 | 1/2004 | Maianti et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0109769 A1 | 6/2004 | Jahn et al. |
| 2004/0115068 A1 | 6/2004 | Hansen et al. |
| 2004/0135078 A1 | 7/2004 | Mandro et al. |
| 2004/0136843 A1 | 7/2004 | Jahn et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0230292 A1 | 10/2005 | Beden et al. |
| 2006/0002823 A1 | 1/2006 | Feldstein |
| 2006/0079766 A1 | 4/2006 | Neer et al. |
| 2006/0079768 A1 | 4/2006 | Beden et al. |
| 2006/0195064 A1 | 8/2006 | Plahey et al. |
| 2007/0040454 A1* | 2/2007 | Freudenberger et al. ...... 310/12 |
| 2007/0112297 A1 | 5/2007 | Plahey et al. |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2007/0278155 A1* | 12/2007 | Lo et al. .................. 210/646 |
| 2008/0033346 A1 | 2/2008 | Childers et al. |
| 2008/0077068 A1 | 3/2008 | Orr |
| 2008/0125693 A1 | 5/2008 | Gavin et al. |

(56) References Cited

U.S. PATENT DOCUMENTS

| | | |
|---|---|---|
| 2008/0208103 A1 | 8/2008 | Demers et al. |
| 2008/0216898 A1 | 9/2008 | Grant et al. |
| 2008/0253912 A1 | 10/2008 | Demers et al. |
| 2009/0004033 A1 | 1/2009 | Demers et al. |
| 2009/0099498 A1 | 4/2009 | Demers et al. |
| 2009/0137940 A1 | 5/2009 | Orr |
| 2009/0169402 A1* | 7/2009 | Stenberg .................. 417/413.1 |
| 2009/0212248 A1* | 8/2009 | Kozak ...................... 251/129.17 |
| 2010/0021313 A1* | 1/2010 | Devan et al. ................ 417/44.1 |
| 2010/0211044 A1* | 8/2010 | Dacquay et al. ............. 604/521 |
| 2010/0241062 A1 | 9/2010 | Morris et al. |
| 2010/0286614 A1* | 11/2010 | Ring ........................... 604/152 |
| 2011/0015610 A1* | 1/2011 | Plahey et al. ................ 604/500 |
| 2011/0020156 A1* | 1/2011 | Van Brunt et al. ........... 417/416 |
| 2011/0092895 A1 | 4/2011 | Yardimci et al. |
| 2011/0125085 A1 | 5/2011 | McGill et al. |
| 2011/0137237 A1 | 6/2011 | Prisco et al. |
| 2011/0152785 A1 | 6/2011 | Chattaraj et al. |
| 2011/0274566 A1* | 11/2011 | Amirouche et al. .......... 417/322 |
| 2011/0293450 A1* | 12/2011 | Grimes et al. ................ 417/420 |
| 2012/0022354 A1* | 1/2012 | Beyer et al. .................. 600/365 |
| 2012/0065581 A1 | 3/2012 | Childers et al. |
| 2012/0073432 A1* | 3/2012 | Ingersoll ............ F04B 43/0054 92/99 |
| 2012/0123322 A1 | 5/2012 | Scarpaci et al. |
| 2012/0209169 A1 | 8/2012 | Morris et al. |
| 2012/0224984 A1 | 9/2012 | Orr |
| 2012/0230844 A1 | 9/2012 | Farrell et al. |
| 2012/0232469 A1 | 9/2012 | Medina |
| 2012/0271226 A1 | 10/2012 | Farrell et al. |
| 2012/0308412 A1 | 12/2012 | Rochat |
| 2013/0118961 A1 | 5/2013 | Beden et al. |
| 2013/0118970 A1 | 5/2013 | Beden et al. |
| 2013/0183170 A1* | 7/2013 | Laermer ....................... 417/313 |
| 2013/0184638 A1 | 7/2013 | Scarpaci et al. |
| 2013/0331774 A1 | 12/2013 | Farrell et al. |

FOREIGN PATENT DOCUMENTS

| | | |
|---|---|---|
| DE | 4006785 | 9/1990 |
| DE | 4336336 | 5/1994 |
| DE | 19837667 | 3/2000 |
| DE | 19919572 A1 | 11/2000 |
| DE | 10042324 | 2/2002 |
| DE | 10046651 | 4/2002 |
| DE | 19919572 C2 | 4/2002 |
| DE | 10053441 | 5/2002 |
| DE | 69618766 | 8/2002 |
| DE | 10143137 | 4/2003 |
| DE | 10157924 | 6/2003 |
| DE | 102007059239 | 6/2009 |
| EP | 0257279 | 3/1988 |
| EP | 0314379 | 8/1991 |
| EP | 0410125 B1 | 8/1993 |
| EP | 0728509 | 8/1996 |
| EP | 0848193 | 6/1998 |
| EP | 0856321 | 8/1998 |
| EP | 0947814 | 10/1999 |
| EP | 0956876 | 11/1999 |
| EP | 1529545 | 5/2005 |
| GB | 1483702 | 8/1977 |
| GB | 2101232 A | 1/1983 |
| GB | 2331796 | 6/1999 |
| JP | 0396850 A | 4/1991 |
| JP | 04191755 | 7/1992 |
| JP | 06154314 | 6/1994 |
| JP | 06002650 | 11/1994 |
| JP | 08028722 | 2/1996 |
| JP | 1068383 A | 3/1998 |
| JP | 11347115 | 12/1999 |
| JP | 2000070358 | 3/2000 |
| JP | 2000346214 | 12/2000 |
| WO | 8402473 | 7/1984 |
| WO | 8601115 | 2/1986 |
| WO | WO9415660 A1 | 7/1994 |
| WO | 9420155 | 9/1994 |
| WO | 9625064 | 8/1996 |
| WO | 9716214 | 5/1997 |
| WO | 9737703 | 10/1997 |
| WO | 9822165 | 5/1998 |
| WO | WO9822167 A1 | 5/1998 |
| WO | 0023140 | 4/2000 |
| WO | 0033898 | 6/2000 |
| WO | 0117605 | 3/2001 |
| WO | 0225146 | 3/2002 |
| WO | 0225225 | 3/2002 |
| WO | WO2007006030 A3 | 6/2007 |
| WO | 2009071069 | 6/2009 |
| WO | WO 2010128914 A1 * | 11/2010 |
| WO | WO2011045167 A1 | 4/2011 |

OTHER PUBLICATIONS

U.S. Appl. No. 13/492,598—Hall Effect Sensor—NPL Wayback Mar. 11, 2011, www.movingmagnet.com, Technologies, Magnetic and Hall effect Postion Sensors.*

Gambro®, "DEHP-free cartridge blood sets," © Nov. 2004, Gambro, Inc., Lakewood, CO, 4 pp.

Gambro®, "Prisma® HF 1000, For Increased Filtration Capacity", © Aug. 2001, Gambro Renal Products, Inc., Lakewood, CO, 2 pp.

Gambro®, "Prisma® M60 and M100 Pre-Pump Infusion Sets— Introducing: The unique solution that enables Physicians to choose a predilution method that meets the needs of their patients", © 2004, Gambro Inc., Lakewood, CO, 4 pp.

Glenn Avolio, "Principles of Rotary Optical Encoders," Sensors Journal of Machine Perception, vol. 10, No. 4, pp. 10-18, 1993.

Manns, Markus et al., "The acu-men: A new device for continuous renal replacement therapy in acute renal failure," Kidney International, vol. 54, pp. 268-274, 1998.

Liberty Cycler Operator's Manual, 2003-2004.

Newton IQ Cycler Operator Manual, Part No. 470203 Rev. F, 2000-2006.

Operator's Instructions, Fresenius 90/2 Peritoneal Therapy Cycler, Part No. 470016, Rev. B, 1991.

Operator's Manual, Serena, Program Version 3.xx—English, 2002.

Sleep Safe Operating Instructions, Software Version 0.9, Part No. 677 801 1; Aug. 2000.

Sleep Safe Technical Manual, Part No. 677 807 1; Aug. 2000.

Bolegoh, Gordon, "Pumps: Reference Guide", p. 24, 3rd edition, 2001.

Ronco et al., "Evolution of Machines for Automated Peritoneal Dialysis", in Automated Peritoneal Dialysis, Contributions to Nephrology, vol. 129, pp. 142-161, 1999.

Sleep Safe Operating Instructions, Software Version 0.5, Apr. 1999.

Sleep Safe Operating Instructions, Software Version 1.0, Oct. 2000.

Sleep Safe Technical Manual, Dec. 2001.

Sleep Safe Operating Instructions, Jan. 2002.

Sleep Safe Communicating Therapy, Mar. 1998.

Sleep Safe Kommunizierte Therapie, May 1998.

Innovative Technologies in Peritoneal Dialysis, Sleep Safe Concept, Oct. 13, 1999 (4 attachments).

TL™ Pump Brochure, TL Systems Corporation.

Gambro®, "Prismaflex™ anticipating critical care needs and taking our innovative response . . . to new heights," © 2004, Gambro Inc., Lakewood, CO, 8 pp.

Greene, Kate, "Robots That Sense Before They Touch", www.technologyreview.com/s/408680/robots-that-sense-before-they-touch/, Sep. 17, 2007, 10 pages.

Smith et al., "Electric Field Imaging Pretouch for Robotic Graspers", manuscript, 8 pages.

* cited by examiner

MEDICAL FLUID CASSETTES AND RELATED SYSTEMS AND METHODS

TECHNICAL FIELD

This disclosure relates to medical fluid cassettes and related systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a medical fluid pumping system includes a medical fluid pumping machine that defines a cassette enclosure and includes a magnetic piston. The system further includes a medical fluid cassette configured to be disposed within the cassette enclosure of the medical fluid pumping machine. The medical fluid cassette includes a base and a magnetically attractive member overlying a fluid pump chamber of the cassette. The magnetically attractive member defines a cavity sized and shaped to receive a portion of the magnetic piston. The cassette is positionable within the cassette enclosure of the medical fluid pumping machine so that the piston is substantially aligned with the fluid pump chamber.

In another aspect of the invention, a medical fluid cassette includes a base and a magnetically attractive member overlying a fluid pump chamber of the cassette. The magnetically attractive member defines a cavity sized and shaped to receive a portion of a piston, and the magnetically attractive member includes a guiding peg configured to be disposed within a cavity of the piston when the piston is coupled to the magnetically attractive member.

In an additional aspect of the invention, a medical fluid pumping system includes a medical fluid cassette defining a fluid pump chamber, a medical fluid pumping machine defining a cassette compartment and including an electromagnetic piston that aligns with the fluid pump chamber of the medical fluid cassette when the medical fluid cassette is disposed in the cassette compartment, a sensor to detect an electrical characteristic indicative of coupling between the electromagnetic piston and the medical fluid cassette, and a controller to apply power to the electromagnetic piston based on the electrical characteristic detected by the sensor.

In yet another aspect of the invention, a medical fluid pumping machine includes an electromagnetic piston, a sensor to detect an electrical characteristic indicative of coupling between the electromagnetic piston and a medical fluid cassette, and a controller to apply power to the electromagnetic piston based on the electrical characteristic detected by the sensor.

In a further aspect of the invention, a method includes supplying electrical power to an electromagnet of a piston, detecting an electrical characteristic of the electromagnet, and determining whether the piston is coupled to a magnetically attractive member of a medical fluid cassette based on the detected electrical characteristic of the electromagnet.

Implementations can include one or more of the following features.

In some implementations, the magnetically attractive member includes a guiding peg extending from a body of the magnetically attractive member.

In some implementations, the body is substantially dome-shaped.

In some implementations, the magnetically attractive member includes a magnetically attractive plate having an aperture sized and shaped to receive the guiding peg.

In some implementations, the magnetically attractive plate is secured to the body of the magnetically attractive member.

In some implementations, the magnetically attractive member includes a magnetically attractive plate secured to a body of the magnetically attractive member.

In some implementations, the magnetically attractive plate is in the form of a disk.

In some implementations, the magnetically attractive plate includes a ferromagnetic material (e.g., steel).

In some implementations, the body is formed of a non-magnetic material (e.g., a polymeric material).

In some implementations, the magnetically attractive member is shaped to substantially conform to a recessed region of the base that forms a portion of the fluid pump chamber.

In some implementations, the magnetically attractive member and the recessed region of the base are substantially dome-shaped.

In some implementations, the piston includes a magnet (e.g., an electromagnet), and the magnetically attractive member includes a material that is attracted to the magnet.

In some implementations, the magnetically attractive member has a substantially flat surface that abuts a substantially flat surface of the piston.

In some implementations, the substantially flat surface of the magnetically attractive member forms an end surface of the cavity.

In some implementations, the magnetically attractive member is attached to a membrane of the cassette.

In some implementations, the piston and the member can be magnetically coupled together with a force of at least about 10 lbf.

In some implementations, the medical fluid pumping machine includes first and second pistons, and the cassette includes first and second magnetically attractive members that overlie first and second fluid pump chambers, respectively. The cassette is positionable within the cassette enclosure of the medical fluid pumping machine so that the first and second pistons substantially align with the first and second fluid pump chambers.

In some implementations, the medical fluid pumping system is a dialysis system (e.g., a peritoneal dialysis system).

In some implementations, the medical fluid cassette is disposable.

In some implementations, the guiding peg extends from a body of the magnetically attractive member.

In some implementations, the cassette includes first and second magnetically attractive members that overlie first and second fluid pump chambers, respectively.

In some implementations, the medical fluid cassette is a dialysis cassette (e.g., a peritoneal dialysis cassette).

In some implementations, the electrical characteristic is voltage across a component of the electromagnetic piston.

In some implementations, the electrical characteristic is frequency of a signal applied to component of the electromagnetic piston.

In some implementations, the electrical characteristic is detected at a wire winding of the electromagnetic piston.

In some implementations, supplying electrical power to the electromagnet includes applying a first current to the electromagnet and, upon detecting an electrical characteristic of the electromagnet, applying a second current to the electromagnet greater than the first current.

In some implementations, the method includes applying a periodic electrical signal to a component of the electromagnet, and detecting an electrical characteristic of the electromagnet includes detecting a characteristic of the periodic electrical signal.

Implementations can include one or more of the following advantages.

In certain implementations, the magnetically attractive member that overlies the pump chamber is magnetically attracted to the piston such that the magnetically attractive member moves in unison with the piston. As a result, when the piston is retracted, the magnetically attractive member moves away from the cassette base causing the volume of the fluid pump chamber to increase and drawing medical fluid into the fluid pump chamber. This arrangement allows the fluid to be drawn into the fluid pump chamber without requiring vacuum pressure to be applied to the membrane. As a result, the complexity and cost of the medical fluid pumping machine can be reduced, and the noise levels resulting from operation of the machine can be reduced relative to vacuum-based systems.

In certain implementations, the magnetically attractive member that overlies the fluid pump chamber defines a recess that is shaped to at least partially receive a piston head of the piston. For example, the magnetically attractive member can include a rigid dome-shaped body and a magnetically attractive disk (e.g., a steel disk) secured within the recess of the body. By positioning the piston head within the recess, movement or slippage (e.g., lateral movement or slippage) of the piston head with respect to the magnetically attractive member can be reduced or minimized.

In some implementations, the magnetically attractive member includes a guiding projection that is sized and shaped to fit within a corresponding cavity in the piston, or vice versa, as the magnetically attractive member and the piston head are coupled to one another. The guiding peg and cavity can help to ensure that the magnetically attractive member and the piston are properly aligned within one another when they become coupled together.

In certain implementations, the magnetically attractive member is retained in a substantially centered position within the pump chamber. This arrangement can help to increase the volumetric accuracy with which the medical fluid pumping system is able to deliver fluid during a treatment cycle.

In some implementations, the piston is equipped with an electromagnet such that the magnetic attraction between the piston and the magnetically attractive member of the cassette can be controlled as desired. This can allow the piston and the magnetically attractive member of the cassette to be selectively coupled and decoupled. In some implementations, for example, the electromagnet can be activated after the cassette has been properly aligned. This can help to ensure that the piston is properly aligned with the fluid pump chamber of the cassette during use and can thus increase pumping accuracy. In some implementations, the electromagnet is deactivated prior to removing the cassette from the medical fluid pumping machine. This can make removal of the cassette from the machine easier while decreasing the risk of tearing the membrane during the decoupling process. Similarly, the strength of the electromagnet can be modulated to adjust the strength of the magnetic attraction between the piston and the magnetically attractive member of the cassette for a given situation.

In implementations in which the magnetically attractive member of the cassette produces its own magnetic field, the current delivered to the electromagnet can be reversed prior to removing the cassette from the machine. Reversing the current in this manner can cause the piston to repel the magnetically attractive member of the cassette, which can facilitate the decoupling and removal process and reduce the risk of damage to the membrane.

In certain implementations, the PD cycler includes a sensor that monitors an electrical characteristic (e.g., a voltage) associated with the electromagnet of the piston. The sensor can be used to determine whether the piston is coupled to or decoupled from the magnetically attractive member of the cassette. Such a sensor can therefore advantageously be used to provide an early indication to the user or to cause the medical fluid pumping machine to take remedial action when the piston becomes decoupled from the magnetically attractive member at an unintended time during use.

Other aspects, features, and advantages will be apparent from the description and drawings, and from the claims.

DETAILED DESCRIPTION

In certain aspects of the invention, a medical fluid cassette (e.g., a dialysis fluid cassette) includes a magnetically attractive member (i.e., a member that is capable of attracting or being attracted to magnets) that is attached to a flexible membrane and overlies a fluid pump chamber of the cassette. The medical fluid cassette is configured to be disposed in a cassette compartment of a medical fluid pumping machine (e.g., a dialysis machine) in a manner such that a piston of the medical fluid pumping machine is substantially aligned with the fluid pump chamber. The piston, which contains a magnet (e.g., an electromagnet), can be partially disposed in a cavity of the magnetically attractive member and can be magnetically coupled to the magnetically attractive member. The medical fluid pumping machine, in certain implementations, includes a sensor (e.g., a current sensor or a voltage sensor) that can be used to detect whether the piston is coupled to or decoupled from the magnetically attractive member.

During use, the coupled piston and magnetically attractive member are advanced to decrease the volume of the fluid pump chamber and force fluid out of the fluid pump chamber. The coupled piston and magnetically attractive member are subsequently retracted to increase the volume of the fluid pump chamber and draw fluid into the fluid pump chamber. By magnetically coupling the magnetically attractive member to the piston, the volume of the fluid pump chamber can be increased by simply retracting the piston. There is typically no need for an external vacuum to be applied to the cassette membrane to increase the volume of the fluid pump chamber. Exemplary medical fluid cassettes, medical fluid pumping machines, medical fluid pumping systems, and medical fluid delivery methods are described below.

Figure 1:
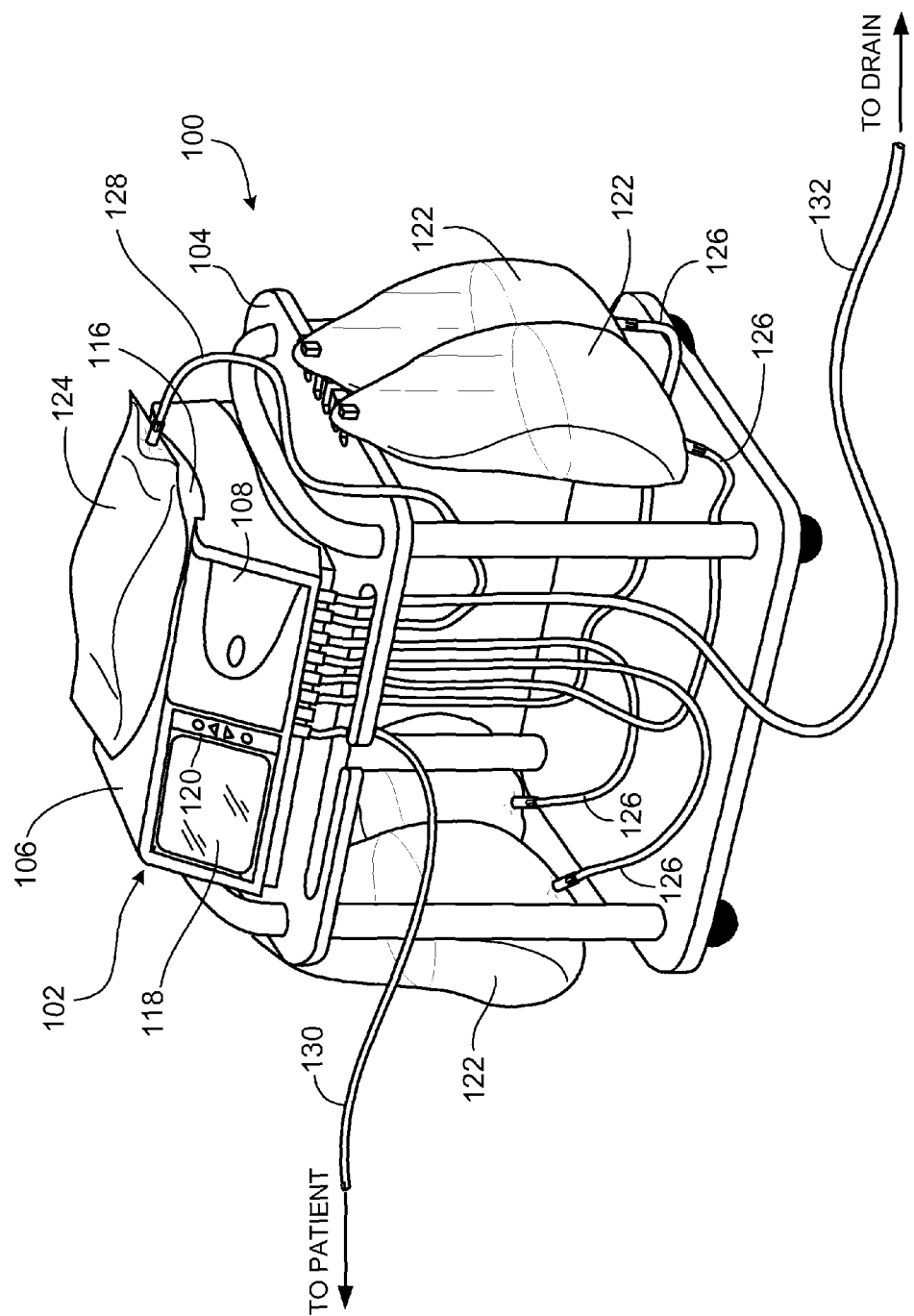
FIG. 1 is a perspective view of a peritoneal dialysis ("PD") system that includes a PD cycler positioned atop a portable cart and a PD cassette positioned in a cassette compartment of the PD cycler.
Figure 2:
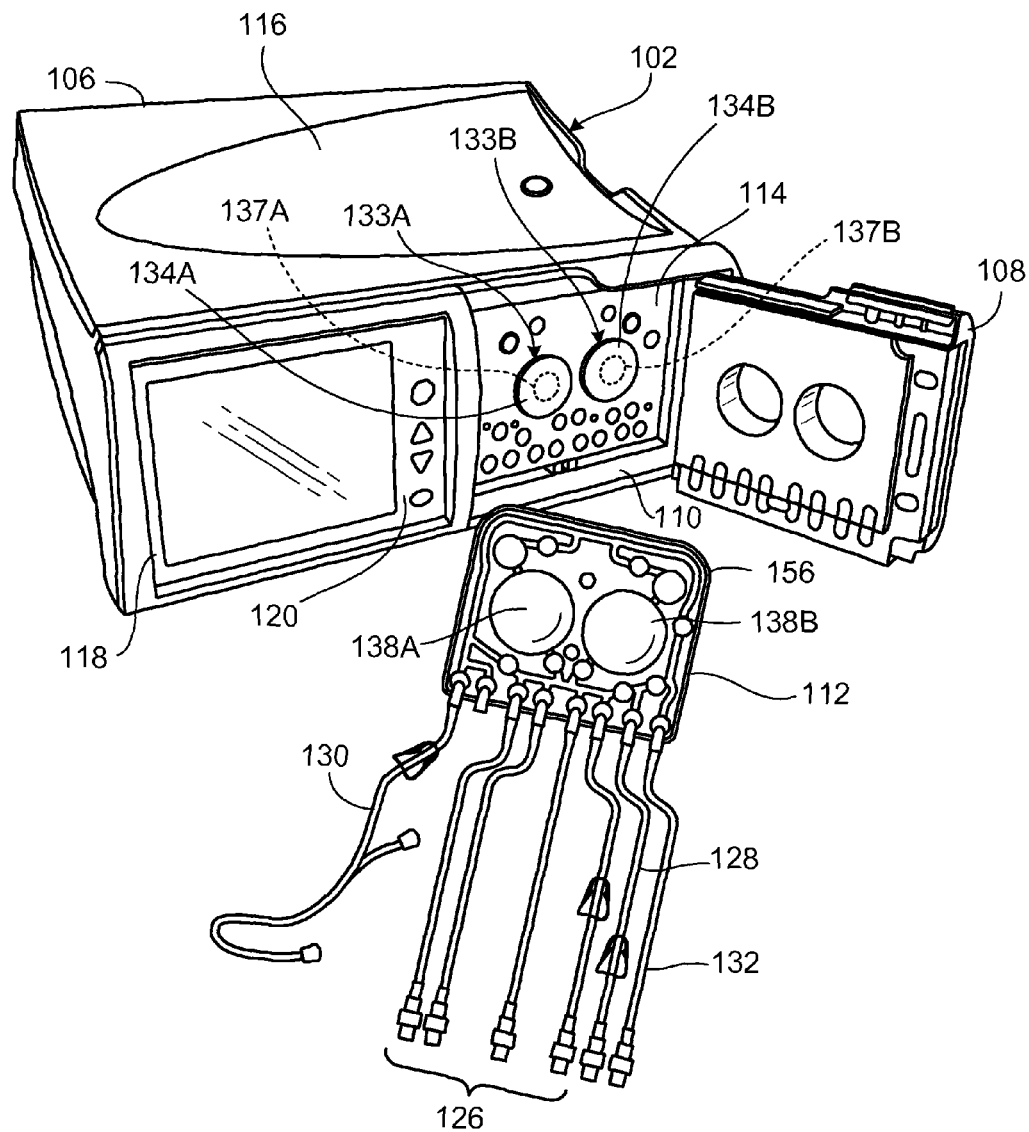
FIG. 2 is a perspective view of the PD system of FIG. 1 with a door of the PD cycler open and the PD cassette removed from the cassette compartment to show the inner surfaces of the PD cycler that interface with the PD cassette during use.

Referring to FIG. 1, a peritoneal dialysis ("PD") system 100 includes a PD cycler (also referred to as a PD machine) 102 seated on a cart 104. Referring also to FIG. 2, the PD cycler 102 includes a housing 106, a door 108, and a cassette interface 110 that mates with a disposable PD cassette 112 when the cassette 112 is disposed within a cassette compartment 114 formed between the cassette interface 110 and the closed door 108. The cassette 112 includes magnetically attractive dome-shaped members 161A, 161B (shown in FIGS. 6 and 8) that overlie recessed regions of a rigid base 156 of the cassette 112 to form fluid pump chambers 138A, 138B.

A heater tray 116 is positioned on top of the housing 106. The heater tray 116 is sized and shaped to accommodate a bag of dialysis solution (e.g., a five liter bag of dialysis solution). The PD cycler 102 also includes a touch screen 118 and additional control buttons 120 that can be operated by a user (e.g., a patient) to allow, for example, set-up, initiation, and/or termination of a PD treatment.

Still referring to FIG. 1, dialysis solution bags 122 are suspended from fingers on the sides of the cart 104, and a heater bag 124 is positioned on the heater tray 116. The dialysis solution bags 122 and the heater bag 124 are connected to the cassette 112 (shown in FIG. 2) via dialysis solution bag lines 126 and a heater bag line 128, respectively. The dialysis solution bag lines 126 can be used to pass dialysis solution from the dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter and can be used to pass dialysis solution back and forth between the cassette 112 and the patient during use. The drain line 132 can be connected to a drain or drain receptacle and can be used to pass dialysis solution from the cassette 112 to the drain or drain receptacle during use.

Figure 3:
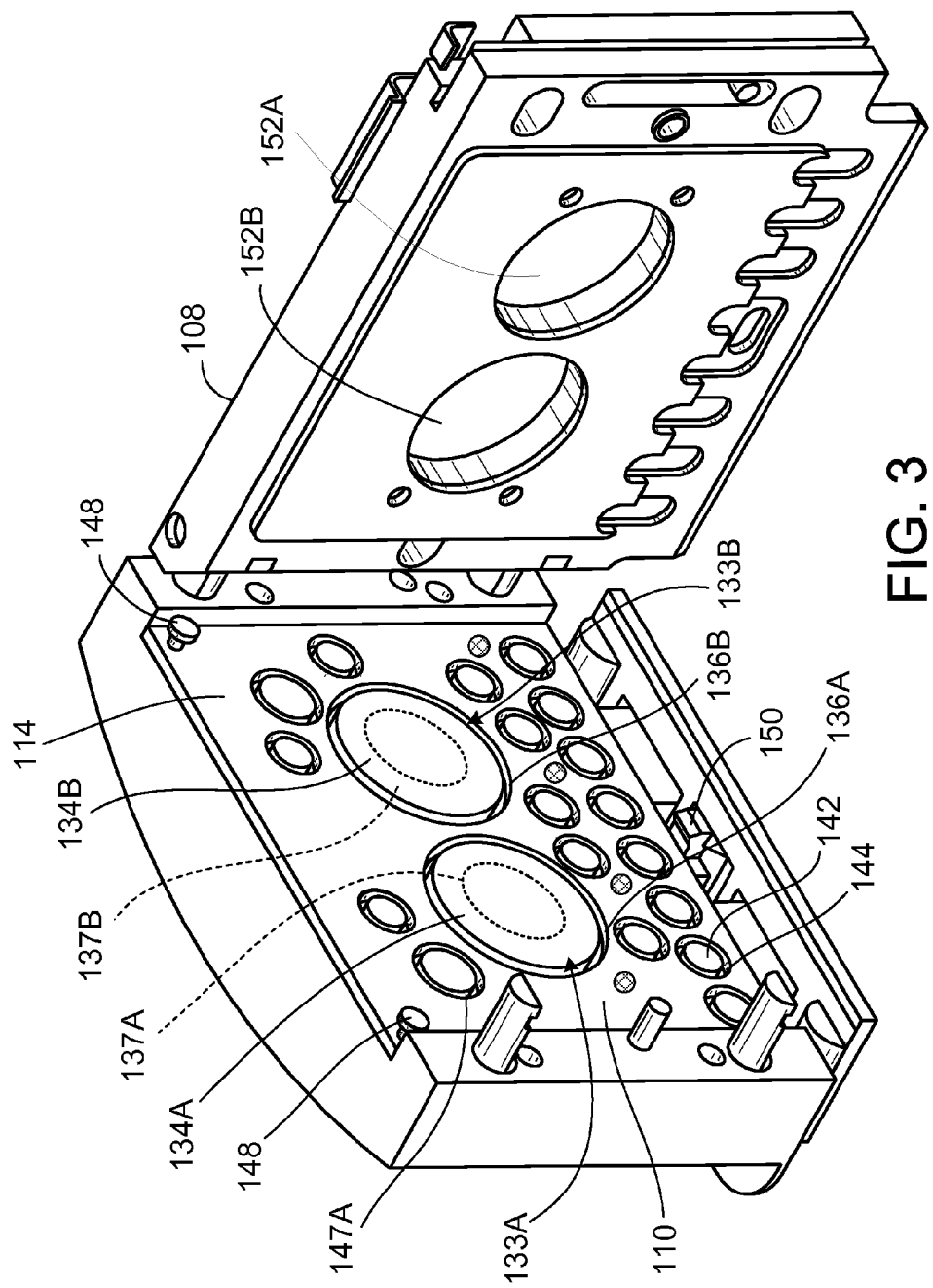
FIG. 3 is a perspective view of the cassette compartment of the PD cycler of FIG. 1.

FIG. 3 shows a more detailed view of the cassette interface 110 and the door 108 of the PD cycler 102. As shown, the PD cycler 102 includes pistons 133A, 133B that contain electromagnets 137A, 137B. The pistons 133A, 133B are connected to a motor (e.g., a stepper motor) positioned in the housing 106 of the PD cycler 102 so that the pistons 133A, 133B can be axially moved within piston access ports 136A, 136B formed in the cassette interface 110. As described in greater detail below, the electromagnetic pistons 133A, 133B can be coupled to the magnetically attractive dome-shaped members 161A, 161B of the cassette 112 when the cassette 112 is disposed within the cassette enclosure 114 during use such that the dome-shaped members 161A, 161B can be reciprocated along with the pistons 133A, 133B.

Figure 4:
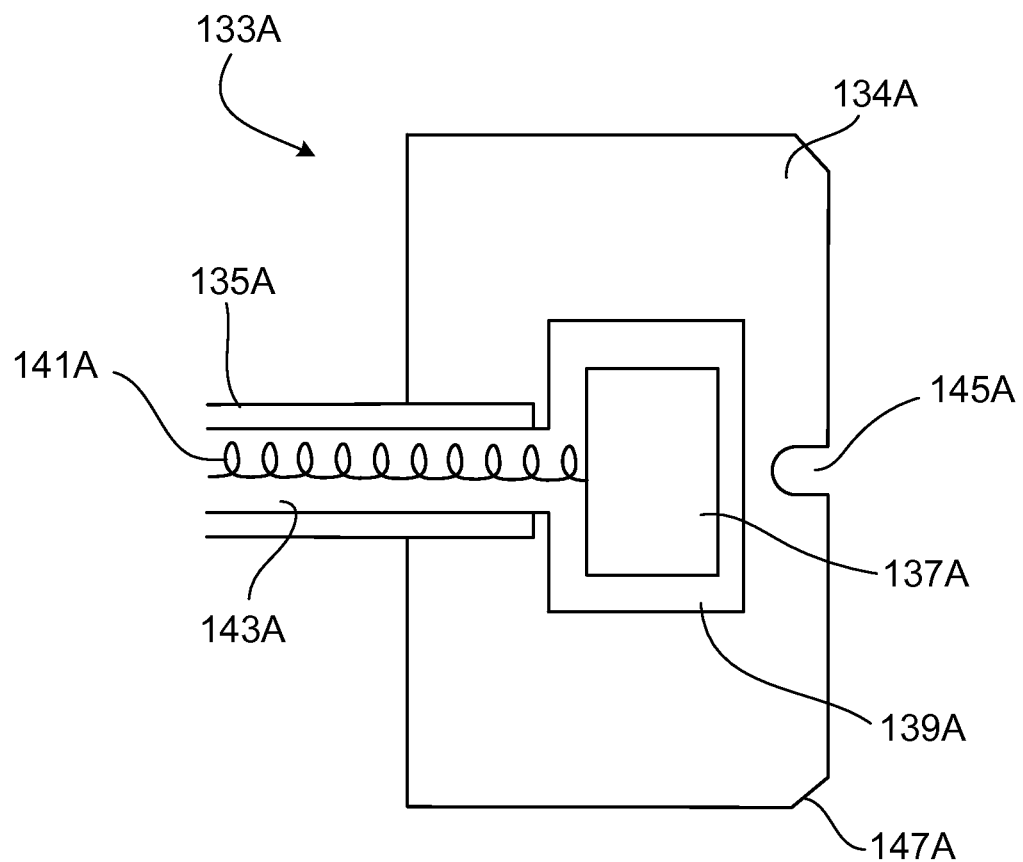
FIG. 4 is a cross-sectional view of an electromagnetic piston assembly of the PD cycler of FIG. 1.

FIG. 4 illustrates a cross-sectional view of the piston 133A. Only the piston 133A and its associated components will be described in detail since the other piston 133B and its associated components have the same construction and operate in the same way as the piston 133A. As shown in FIG. 4, the piston 133A includes a piston head 134A that is attached to a piston shaft 135A. The piston head 134A is a generally cylindrical member that defines a central cavity 139A in which the electromagnet 137A is disposed. A coiled wire (e.g., a coiled copper wire) 141A extending from the electromagnet 137A passes through a channel 143A formed in the piston shaft 135A and connects to a power source located within the housing of the PD cycler 102. As will be discussed in greater detail below, electrical power can be delivered via the coiled wire 141A from the power source to the electromagnet 137A in order to magnetize the electromagnet 137A.

The front face of the piston head 134A forms a guiding cavity 145A that is sized and shaped to receive a guiding peg 169A of the dome-shaped member 161A. The cavity 145A and the guiding peg 169A are similarly shaped such that they mate when the piston 133A is fully advanced and in contact with the dome-shaped member 161A of the cassette 112. If the guiding peg 169A and the cavity 145A are slightly misaligned as the piston 133A is axially moved into contact with the dome-shaped member 161A of the cassette 112, the curved outer surface of the guiding peg 169A will cause the guiding peg 169A to ride along the wall of the cavity 145A until the guiding peg 169A is centered within the cavity 145A. As a result, the dome-shaped member 161A of the cassette 112 will shift slightly to be centered over the piston head 134A.

The front circumferential edge 147A of the piston head 134A is chamfered. The chamfered edge 147A cooperates with a chamfered circumferential edge of the dome-shaped member 161A to ensure that the piston head 134A and the dome-shaped member 161A are properly aligned within one another when fully engaged.

The body of the piston head 134A typically has an outer diameter that is only slightly smaller (e.g., about 0.250 inch to about 0.375 inch smaller) than the diameter of the recess formed by the associated magnetically attractive dome-shaped member 161A such that at least a portion of the piston head 134A can be received in the recess of the dome-shaped member 161A. In some implementations, the piston head has a diameter of about 1.0 inch to about 3.0 inch (e.g., about 1.625 inch to about 1.75 inch, about 2.0 inch).

The piston head 134A and the piston shaft 135A are typically formed of one or more non-magnetic materials. In some implementations, these piston components are formed of aluminum. Other metals, such as brass, bronze, non-magnetic stainless steel, and titanium, can alternatively or additionally be used to form the piston head 134A and the piston shaft 135A. Alternatively, certain plastics, such as ABS, Delrin, polycarbonate, PEEK, fiber-reinforced PEEK, carbon fiber, nylon, Ultem, PVC, and PPC, can be used to form the piston head 134A and the piston shaft 135A.

In some cases, the piston head 134A includes two halves that are separately molded. After forming the two halves of the piston head 134A, the electromagnet 137A is positioned within a recess formed in the first half. The second half of the piston head is then positioned adjacent the first half such that a recess formed in the second half aligns with the recess formed in the first half to define the cavity 139A in which the electromagnet 137A is contained. After aligning the piston head halves in this way, they are bonded (e.g., thermally bonded or adhesively bonded) together to form the piston head 134A.

When electrical power is supplied from the power source to the electromagnet 137A, the electromagnet 137A becomes magnetized, and when electrical power is not being supplied to the electromagnet 137A, the electromagnet 137A is not magnetized. The electromagnet 137A can be any of various different types of electromagnets that are capable of providing the desired coupling force (e.g., a 10-50 pound coupling force) between the piston 133A and the dome-shaped member 161A of the cassette 112. Typically, the electromagnet 137A includes a core (e.g., a steel or iron core) about which a portion of the wire 141A is wound. The core and the wire winding are typically contained within a housing. Examples of suitable electromagnets include the R-1012-12 and the R-1207-12 electromagnets available from Magnetech Corporation. Another example of a suitable electromagnet is the EM050-12-222 electromagnet available from APW Company (Rockaway, N.J.). It should be understood, however, that other electromagnets can alternatively or additionally be used.

The piston shaft 135A is secured at one end to the body of the piston head 134A and at its opposite end to the motor in the housing 106 of the PD cycler 102. Typically, the piston shaft 135A is thermally bonded to the piston head 134A. However, any of various other types of coupling methods, including adhesive, mechanical fastening, etc., can alternatively or additionally be used to secure the piston shaft 135A to the piston head 134A. Similarly, any of various suitable connection mechanisms, such as lead screw mechanisms, ball screw mechanisms, or other gear-type mechanisms, can be used to connect the piston shaft 135A to the motor. Operation of the motor causes the piston 133A to reciprocate within the piston access port 136A formed in the cassette interface 110 (shown in FIG. 3). As the piston 133A reciprocates, the coiled geometry of the wire 141A allows the wire 141A to resiliently increase and decrease in length without breaking or becoming damaged.

As will be discussed in greater detail below, when the cassette 112 (shown in FIGS. 6-8) is positioned within the cassette compartment 114 and the door 108 is closed, the electromagnetic pistons 133A, 133B of the PD cycler 102 align with the pump chambers 138A, 138B of the cassette 112 such that, upon supplying a desired level of electrical power to the electromagnets 137A, 137B of the pistons 133A, 133B, the magnetically attractive dome-shaped members 161A, 161B overlying the pump chambers 138A, 138B become magnetically coupled to the pistons 133A, 133B. The pistons 133A, 133B, the dome-shaped members 161A, 161B, and the portions of the cassette membrane 140 that immediately surround the dome-shaped members 161A, 161B can be advanced to decrease the volume defined by the pump chambers 138A, 138B and force dialysis solution out of the pump chambers 138A, 138B, and can then be retracted to decrease the volume defined by the pump chambers 138A, 138B and draw dialysis solution into the pump chambers 138A, 138B.

The power source that supplies power to the electromagnet 137A is typically a main power supply for the PC cycler 102. In some examples, the main power supply draws power from an alternating current (AC) source (e.g., a conventional power outlet accessible at a wall of a building) and provides direct current (DC) power to components of the PD cycler 102 including the electromagnet 137A. In some implementations, the electromagnet 137A operates at 24 Volts and draws between 200 and 400 mA of current. If the main power supply for the PD cycler 102 supplies a voltage other than the voltage at which the electromagnet 137A operates then a transformer could be used to step up or step down the voltage of the main power supply to an operational voltage (e.g., 24V) of the electromagnet 137A.

The PD cycler 102 is also equipped with a voltage sensor that is connected to the wire 141A. The voltage sensor can, for example, be a discrete component such as a single integrated circuit encapsulated in a circuit package. Other types of voltage sensors can be used, for example, a voltage sensing circuit having multiple components such as diodes, transistors, analog-to-digital converters, and/or other kinds of components. As discussed below, the voltage sensor can be used to determine whether the piston 133A, 133B is coupled to or decoupled from the dome-shaped member 161A of the cassette 112. It should be understood that a similar voltage sensor is connected to the wire winding of the electromagnetic positioned in the other piston 133B.

Figure 5:
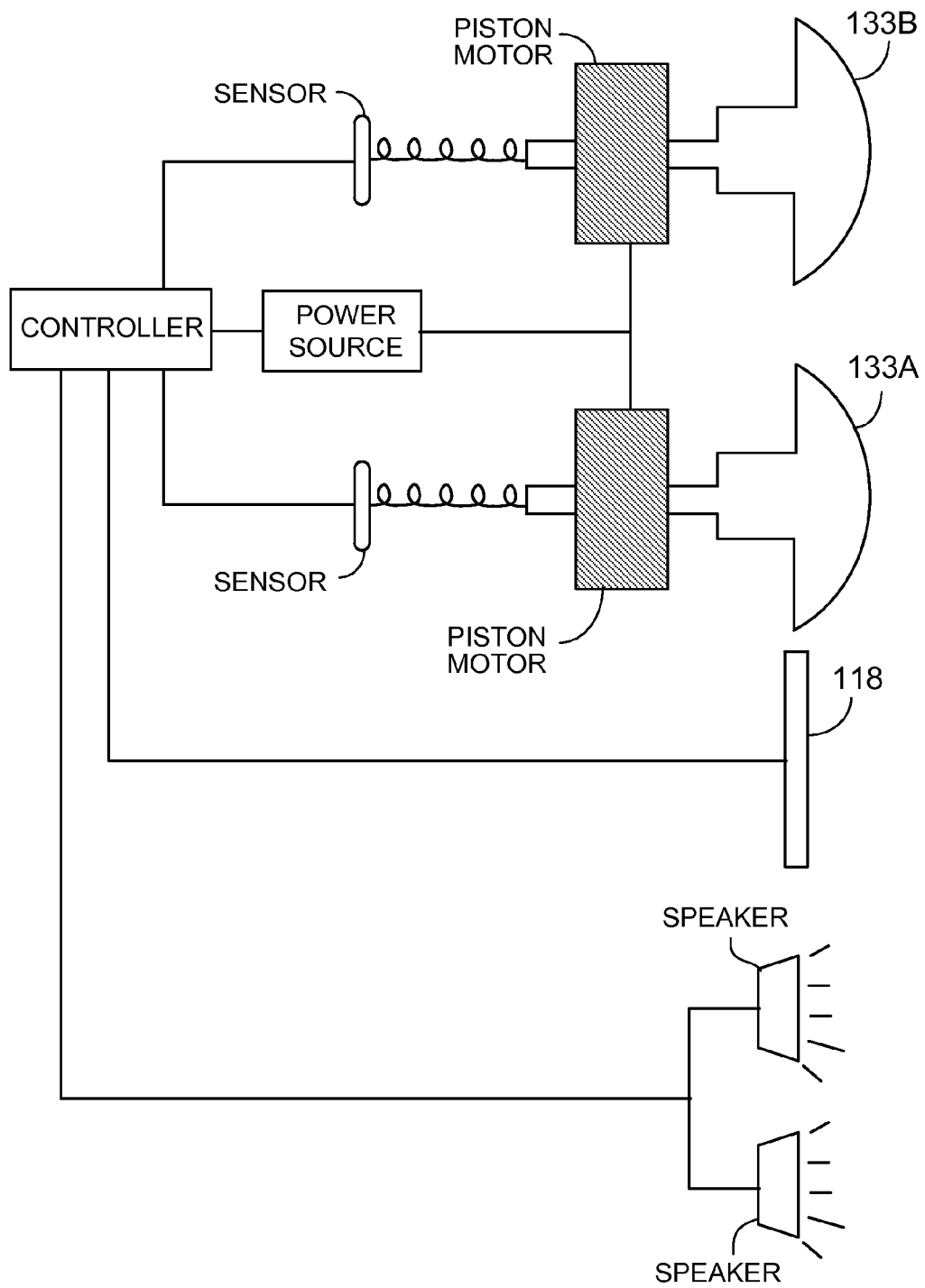
FIG. 5 is a schematic of various electronic components of the PD cycler of FIG. 1.

As schematically illustrated in FIG. 5, the power source, the voltage sensor, the piston motors, the display unit 118, and speakers of the PD cycler 102 are electrically connected to a controller (e.g., a microprocessor). Conventional electrical wires or lead lines can be used to connect these components to the controller. The controller includes a memory that stores instructions for operating the PD cycler based on feedback received from the voltage sensor. The supply of electrical power to the electromagnet 137A can be controlled in such a way to gradually increase or decrease the magnetic force of the electromagnet during use. For example, as the piston 133A is advanced toward the cassette 112 to couple the piston 133A to the magnetically attractive dome-shaped member 161A, a relatively low current (e.g., about 50 to 150 mA for an electromagnet that operates at 200 mA when operating at full power) is typically applied to the electromagnet 137A via the wire 141A to generate a relatively low magnetic force. The magnetic force can be maintained at this low level until the piston 133A is coupled to the magnetically attractive dome-shaped member 161A of the cassette 112. By maintaining the magnetic force at this low level, a violent coupling process can be avoided. Instead, the low magnetic force causes the magnetically attractive dome-shaped member 161A to be lightly drawn toward and coupled to the piston 133A.

In some implementations, the relatively low current is achieved using a technique such as pulse-width modulation (PWM). When PWM is used, the voltage applied to the electromagnet 137A is switched on and off at a high frequency over a period of time. Because the voltage applied to the electromagnet 137A is not constant, the average current applied to the electromagnet 137A drops in proportion to the amount of time the voltage is switched on. For example, if the voltage is switched on 50% of the time and switched off 50% of the time, then the average current applied to the electromagnet 137A will be 50% of the current applied to the electromagnet 137A when PWM is not used. If the current applied to the electromagnet 137A is 200 mA when a constant voltage of 24V is used, for example, then the current applied to the electromagnet 137A using the 50% on, 50% off PWM technique will be 100 mA. In some implementations, a constant voltage supplied by a power source can be applied to a PWM circuit to generate a PWM signal, and the PWM signal can be applied to the electromagnet 137A as its voltage source.

The voltage sensor monitors the voltage across the wire winding surrounding the core of the electromagnet 137A and regularly transmits a signal indicative of that measured voltage to the controller. As the magnetically attractive dome-shaped member 161A and the piston 133A become coupled together, the voltage sensor detects a change (e.g., a spike) in the voltage across the wire winding. For example, when the magnetically attractive dome-shaped member 161A and the piston 133A become coupled together, the presence of the magnetically attractive dome-shaped member 161A may change the inductance of the electrical circuit that includes the wire winding. When the inductance of the electrical circuit changes, the voltage across the wire winding will also change. The sensor transmits a signal including the measured voltage to the controller. The controller is programmed to determine, based on the signal received from the voltage sensor, whether the piston is coupled to the magnetically attractive dome-shaped member of the cassette or decoupled from the magnetically attractive dome-shaped member of the cassette. For example, the controller can include a look-up table of empirical data showing, for various different currents applied to the electromagnet, the average voltage measured across the winding of the electromagnet when the piston is coupled to the magnetically attractive dome-shaped member of the cassette and the average voltage measured across the winding of the electromagnet when the piston is decoupled from the magnetically attractive dome-shaped member of the cassette. The controller knows the current being applied to the electromagnet and can thus determine from the empirical data of the look-up table whether the piston is coupled or decoupled at any particular time.

In response to receiving the voltage signal from the sensor indicating that the initial coupling between the piston and the magnetically attractive dome-shaped member has occurred, the controller increases the current supplied to the electromagnet 137A to create a stronger coupling between the magnetically attractive dome-shaped member 161A and the piston 133A. The current can, for example, be increased to about 200 mA to 400 mA, depending on the full-power current of the electromagnet 137A (which is typically a characteristic of the electromagnet provided by the manufacturer of the electromagnet). The stronger coupling force that occurs as a result of the increased current can, for example, be used during fluid pumping to better ensure that the piston 133A and the magnetically attractive dome-shaped member 161A do not inadvertently become decoupled during the pumping process.

The voltage sensor also monitors the voltage across the winding of the electromagnet 137A throughout the pumping process. Thus, in the event that the piston 133A becomes inadvertently decoupled from the magnetically attractive dome-shaped member 161A during the pumping process, the voltage sensor will detect a change in the voltage across the winding and will transmit a signal indicative of a decoupling to the controller. Upon determining that the piston 133A has become decoupled from the magnetically attractive dome-shaped member 161A of the cassette 112 during a phase of operation in which the piston 133A is expected to be coupled to the magnetically attractive dome-shaped member 161A, the controller can activate an alarm (e.g., a visual alarm displayed on the display 120 of the PD cycler 102 and/the pdio alarm emitted from speakers of the PD cycler 102) to inform the user that the piston has become decoupled. Alternatively or additionally, the controller can attempt to re-couple the piston 133A with the magnetically attractive dome-shaped member 161A by applying a voltage to the electromagnet 137A in the manner described above.

The controller controls the piston motor throughout the pumping process and thus knows when the pumping process is complete. For a particular treatment, for example, the controller will typically be programmed to reciprocate the piston 133A a given number of times to cause a desired volume of dialysis solution to be pumped to the patient and drawn from the patient. Upon completion of the pumping process, the piston 133A is decoupled from the magnetically attractive dome-shaped member 161A of the cassette 112. To decouple these components, the controller causes the power source to stop delivering electrical power to the electromagnet 137A and the piston 133A is retracted out of contact with the magnetically attractive dome-shaped member 161A. Because electrical power is no longer being delivered to the electromagnet 137A, the piston 133A is free to retract without resistance caused by a magnetic attraction between the piston 133A and the magnetically attractive dome-shaped member 161A.

Referring again to FIG. 3, the PD cycler 102 also includes multiple inflatable members 142 positioned within inflatable member access ports 144 in the cassette interface 110. The inflatable members 142 align with depressible dome regions 146 of the cassette 112 (shown in FIG. 6) when the cassette 112 is positioned within the cassette compartment 114. While only one of the inflatable members 142 is labeled in FIG. 3, it should be understood that the PD cycler 102 includes an inflatable member 142 associated with each of the depressible dome regions 146 of the cassette 112. The inflatable members 142 act as valves to direct dialysis solution through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member access ports 144 and out of contact with the cassette 112 when deflated. By inflating certain inflatable members 142 to depress their associated dome regions 146 on the cassette 112, certain fluid flow paths within the cassette 112 can be occluded. Thus, dialysis solution can be pumped through the cassette 112 by actuating the pistons 133A, 133B, and can be guided along desired flow paths within the cassette 112 by selectively inflating and deflating the inflatable members 142.

Still referring to FIG. 3, locating pins 148 extend from the cassette interface 110. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a tab 150 extending from the cassette interface 110 to allow the door 108 to be closed over the cassette 112. The locating pins 148 help to ensure that the pump chambers 138A, 138B of the cassette 112 are aligned with the pistons 133A, 133B when the cassette 112 is positioned in the cassette compartment 114 between the closed door 108 and the cassette interface 110.

The door 108, as shown in FIG. 3, defines recesses 152A, 152B that substantially align with the pistons 133A, 133B when the door 108 is in the closed position. When the cassette 112 is positioned within the cassette compartment 114, hollow projections 154A, 154B of the cassette 112 (shown in FIG. 7), inner surfaces of which cooperate with the dome-shaped members 161A, 161B and portions of the membrane 140 surrounding the dome-shaped members 161A, 161B to form the pump chambers 138A, 138B, fit within the recesses 152A, 152B. The door 108 further includes a pad that can be inflated during use to compress the cassette 112 between the door 108 and the cassette interface 110. With the pad inflated, the portions of the door 108 forming the recesses 152A, 152B support the projections 154A, 154B and the planar surface of the door 108 supports the other regions of the cassette 112. The door 108 can counteract the forces applied by the pistons 133A, 133B and the inflatable members 142 and thus allows the pistons 133A, 133B to depress the portions of the membrane 140 overlying the pump chambers 138A, 138B and similarly allows the inflatable members 142 to actuate the depressible dome regions 146 on the cassette 112.

The PD cycler 102 includes various other features not described in detail herein. Further details regarding the PD cycler 102 and its various components can be found in U.S. Patent Application Publication No. 2007/0112297, which is incorporated by reference herein.

Figure 6:
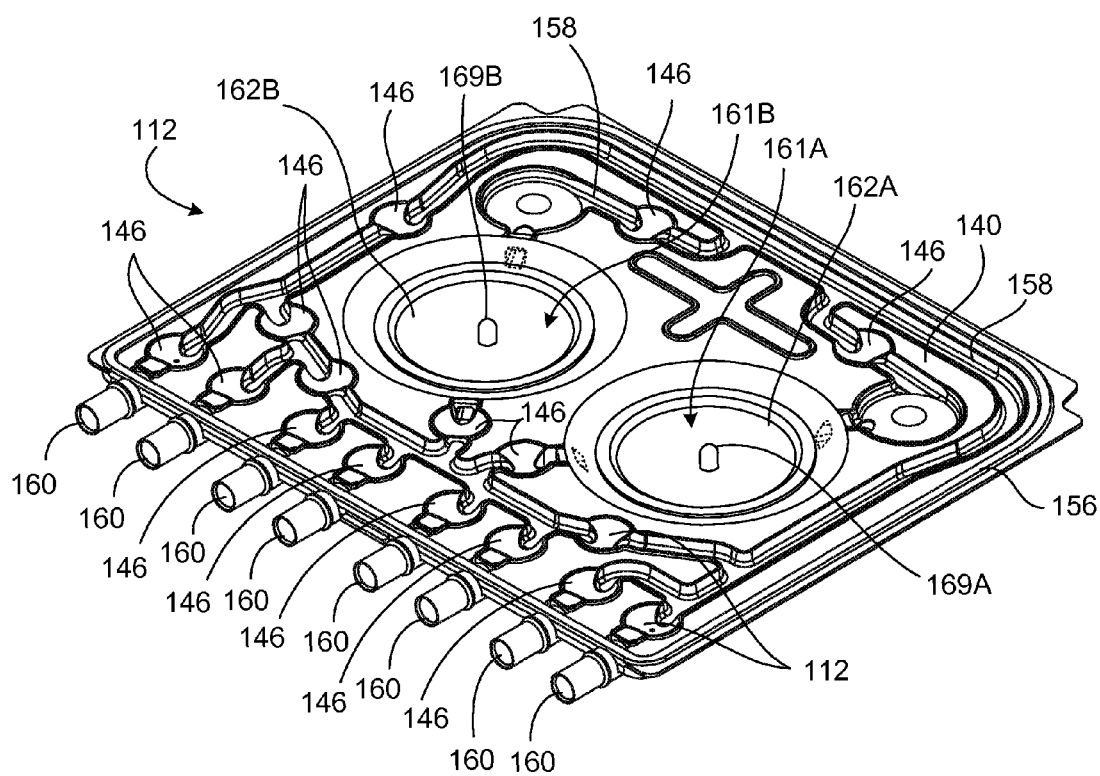
FIGS. 6 and 7 are perspective views of the PD cassette of the PD system of FIG. 1, from a flexible membrane side of the PD cassette and from a rigid base side of the PD cassette, respectively. The PD cassette includes magnetically attractive dome-shaped members overlying pump chambers of the cassette.
Figure 7:
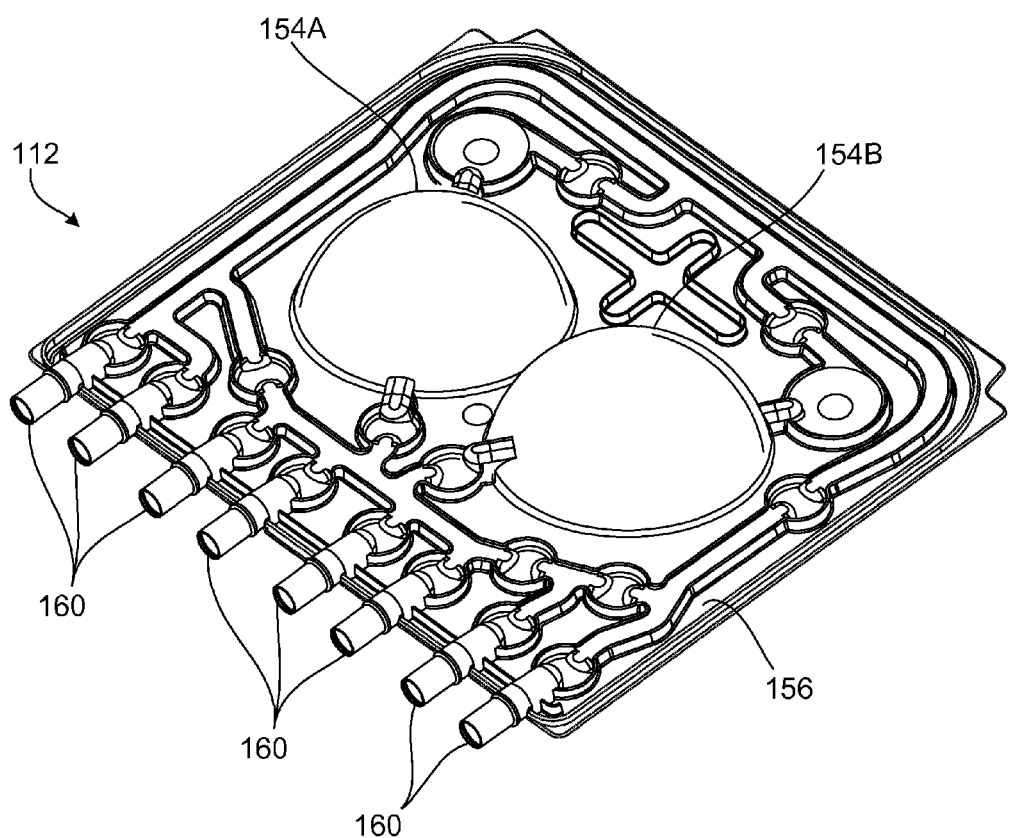
Figure 8:
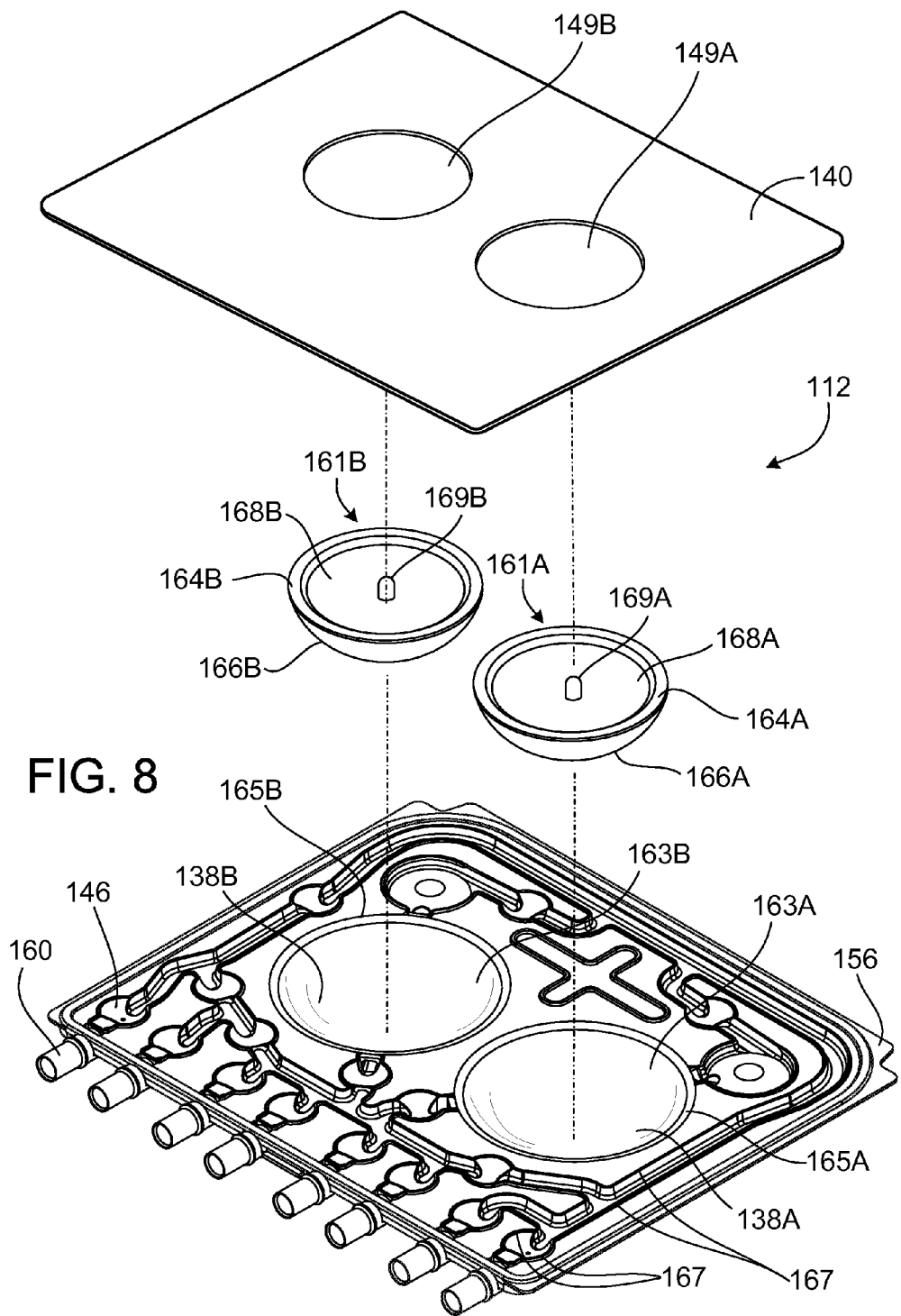
FIG. 8 is an exploded, perspective view of the PD cassette of the PD system of FIG. 1.

FIGS. 6 and 7 are perspective views from the membrane side and rigid base side, respectively, of the cassette 112, and FIG. 8 is an exploded, perspective view of the cassette 112. As shown in FIGS. 6-8, the cassette 112 includes the tray-like rigid base 156, the flexible membrane 140, which is attached to the periphery of the base 156, and the magnetically attractive dome-shaped members 161A, 161B, which are aligned with cut-outs 149A, 149B formed in the membrane 140 and overlie recessed regions 163A, 163B formed by the hollow projections 154A, 154B of the base 156. The recessed regions 163A, 163B of the base 156 cooperate with the dome-shaped members 161A, 161B and portions of the flexible membrane 140 surrounding the dome-shaped members 161A, 161B to form the pump chambers 138A, 138B when the cassette 112 is compressed between the door 108 and the cassette interface 110 of the PD cycler 102 resulting in the flexible membrane 140 being pressed against raised ridges 165A, 165B that extend from the base 156 and surround the recessed regions 163A, 163B. The volumes between the hollow projections 154A, 154B that form the recessed regions 163A, 163B of the base 156 and the dome-shaped members 161A, 161B and membrane 140 serve as the pump chambers 138A, 138B.

The dome-shaped members 161A, 161B include rigid plastic dome-shaped bodies 166A, 166B that are shaped to generally conform to the recessed regions 163A, 163B of the base 156 of the cassette 112. Annular flanges 164A, 164B extend from top surfaces (in the view shown in FIG. 8) of the dome-shaped bodies 166A, 166B. The annular flanges 164A, 164B have flat surfaces that are attached (e.g., thermally or adhesively bonded) to the inner surface of portions of the membrane 140 that surround the dome-shaped members 161A, 161B and overlie the pump chambers 138A, 138B.

The flat upper surfaces (in the view shown in FIG. 8) of the dome-shaped bodies 166A, 166B and the flanges 164A, 164B define central cavities 168A, 168B that are sized and shaped to receive end portions of the piston heads 134A, 134B. The cavities 168A, 168B can, for example, have depths of about 0.1 inch to about 0.15 inch and diameters of about 1.625 inch to about 1.725 inch. The annular flanges 164A, 164B have chamfered inner edges surrounding the cavities 168A, 168B. The chamfered inner edges can facilitate alignment between the pistons 133A, 133B and the magnetically attractive dome-shaped members 161A, 161B by ensuring that the pistons are guided into the central cavities 164A, 164B as the pistons 133A, 133B are being coupled to the magnetically attractive dome-shaped members 161A, 161B.

Guiding pegs 169A, 169B extend upward from the bottom surfaces of the cavities (in the view shown in FIG. 8). The guiding pegs 169A, 169B are sized and shaped to fit within the guiding cavities 145A, 145B formed in the piston heads 134A, 134B of the pistons 133A, 133B. The guiding pegs 169A, 169B can, for example, extend to a height of about 0.1 inch to about 0.15 inch above the bottom surfaces of the central cavities 168A, 168B and can have diameters of about 0.1 inch to about 0.15 inch. The tops of the guiding pegs 169A, 169B are rounded (or dome-shaped) to assist in guiding the guiding pegs 169A, 169B into the guiding cavities 145A, 145B of the piston heads 134A, 134B.

The dome-shaped bodies 166A, 166B, the flanges 164A, 164B, and the guiding pegs 169A, 169B are typically integrally formed with one another. For example, these components can be formed using injection molding techniques. Alternatively, other techniques, such as machining or etching techniques, can be used to form the dome-shaped bodies 166A, 166B, the flanges 164A, 164B, and the guiding pegs 169A, 169B. Typically, these components of the dome-shaped members 161A, 161B are formed of polypropylene. However, one or more other biocompatible polymers can alternatively or additionally be used. In certain implementations, these components of the dome-shaped members 161A, 161B are formed of polyoxymethylene (marketed under the trade name Delrin available from Dupont of Wilmington, Del.). Other suitable biocompatible polymers include polytetrafluoroethylene (PTFE), polyvinyl chloride, polycarbonate, and polysulfone.

Magnetically attractive, steel disks 162A, 162B are disposed within the cavities 168A, 168B and are attached (e.g., thermally bonded) to the adjacent flat surfaces of the dome-shaped bodies 166A, 166B. The steel disks 162A, 162B include central apertures that receive the guiding pegs 169A, 169B extending from the dome-shaped bodies 166A, 166B. The interaction between the apertures and the guiding pegs 169A, 169B ensure that the steel disks 162A, 162B are substantially centered within the cavities 168A, 168B.

Because the steel disks 162A, 162B are aligned with the ends of the pistons 133A, 133B, the magnetically attractive dome-shaped members 161A, 161B are drawn against the piston heads 134A, 134B when the electromagnets 137A, 137B of the pistons 133A, 133B are energized. Due to this construction, the pistons 133A, 133B can be used to advance the dome-shaped members 161A, 161B toward the base 156 and thus decrease the volume of the pump chambers 138A, 138B, or to retract the dome-shaped members 161A, 161B away from the base 156 of the cassette 112 and thus increase the volume of the pump chambers 138A, 138B. Decreasing the volume of the pump chambers 138A, 138B causes fluid (e.g., about 12-13 ml of fluid) to be expelled from the pump chambers 138A, 138B via fluid outlet ports, while increasing the volume of the pump chambers 138A, 138B causes fluid (e.g., about 12-13 ml of fluid) to be drawn into the pump chambers 138A, 138B via fluid inlet ports.

While the magnetically attractive disks 162A, 162B have been described as being formed of steel, one or more other ferromagnetic materials can alternatively or additionally be used. Other examples of ferromagnetic materials from which the magnetically attractive disk 162A can be formed include stainless steel, iron, nickel, and cobalt. The thickness of the magnetically attractive disk 162A depends on the type of material from which the magnetically attractive disk 162A is formed and the desired magnetic force to be applied between the disk 162A and the piston 133A. In some implementations, the disk 162A has a thickness of about 0.020 inch to about 0.060 inch (e.g., about 0.040 inch). In certain implementations, the magnetically attractive disk 162A is itself a magnet.

Referring again to FIGS. 6-8, the membrane 140, when compressed against the base 156, contacts the raised ridges 165A, 165B surrounding the recessed regions 163A, 163B of the base 156 to form a liquid-tight seal around the pump chambers 138A, 138B. The membrane 140 also cooperates with a series of raised ridges 167 extending from the base 156 to form a series of fluid pathways 158 and to form the multiple, depressible dome regions 146, which are widened portions (e.g., substantially circular widened portions) of the fluid pathways 158. During use, the dialysis solution flows to and from the pump chambers 138A, 138B through the fluid pathways 158 and dome regions 146. At each depressible dome region 146, the membrane 140 can be deflected to contact the surface of the base 156 from which the raised ridges 167 extend. Such contact can substantially impede (e.g., prevent) the flow of dialysis solution along the region of the pathway 158 associated with that dome region 146 during use. Thus, as described in further detail below, the flow of dialysis solution through the cassette 112 can be controlled through the selective depression of the depressible dome regions 146 by selectively inflating the inflatable members 142 of the PD cycler 102.

The rigidity of the base 156 helps to hold the cassette 112 in place within the cassette compartment 114 of the PD cycler 102 and to prevent the base 156 from flexing and deforming in response to forces applied to the projections 154A, 154B by the dome-shaped members 161A, 161B and in response to forces applied to the planar surface of the base 156 by the inflatable members 142.

The base 156 can be formed of any of various relatively rigid materials. In some implementations, the base 156 is formed of one or more polymers, such as polypropylene, polyvinyl chloride, polycarbonate, polysulfone, and other medical grade plastic materials. In certain implementations, the base 156 is formed of one or more metals or alloys, such as stainless steel. The base 156 can alternatively be formed of various different combinations of the above-noted polymers and metals. The base 156 can be formed using any of various different techniques, including machining, molding, and casting techniques.

Still referring to FIGS. 6-8, fluid line connectors 160 are positioned along the bottom edge of the cassette 112. The fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysis solution bag lines 126, the heater bag line 128, the patient line 130, and the drain line 132. One end of the fitting can be inserted into and bonded to its respective line and the other end can be inserted into and bonded to its associated connector 160. By permitting the dialysis solution bag lines 126, the heater bag line 128, the patient line 130, and the drain line 132 to be connected to the cassette 112, as shown in FIGS. 1 and 2, the connectors 160 allow dialysis solution to flow into and out of the cassette 112 during use.

As noted above, the membrane 140 is attached to the periphery of the base 156. The portion of the membrane 140 overlying the central portion of the base 156 is typically not attached to the base 156. Rather, this portion of the membrane 140 sits loosely atop the raised ridges 165A, 165B, and 167 extending from the planar surface of the base 156. Any of various attachment techniques, such as adhesive bonding and thermal bonding, can be used to attach the membrane 140 to the periphery of the base 156. The thickness and material(s) of the membrane 140 are selected so that the membrane 140 has sufficient flexibility to flex toward the base 156 in response to the force applied to the membrane 140 by the pistons 133A, 133B and the inflatable members 142. In certain implementations, the membrane 140 is about 0.100 micron to about 0.150 micron in thickness. However, other thicknesses may be sufficient depending on the type of material used to form the membrane 140.

Any of various different materials that permit the membrane 140 to deflect in response to movement of the pistons 133A, 133B and inflation of the inflatable members 142 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062(SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane can alternatively include more or fewer layers and/or can be formed of different materials.

The rigid base 156, the membrane 140, and the dome-shaped members 161A, 161B are typically formed separately and then assembled to make the cassette 112. In some implementations, for example, after forming the rigid base 156 and the dome-shaped members 161A, 161B, the dome-shaped members 161A, 161B are attached (e.g., welded) to the portions of the membrane 140 surrounding the cut-outs 149A, 149B and then inserted into the recesses 163A, 163B formed by the hollow protrusions 154A, 154B of the rigid base 156. The membrane 140 is then attached to the perimeter of the rigid base 156.

Figure 9:
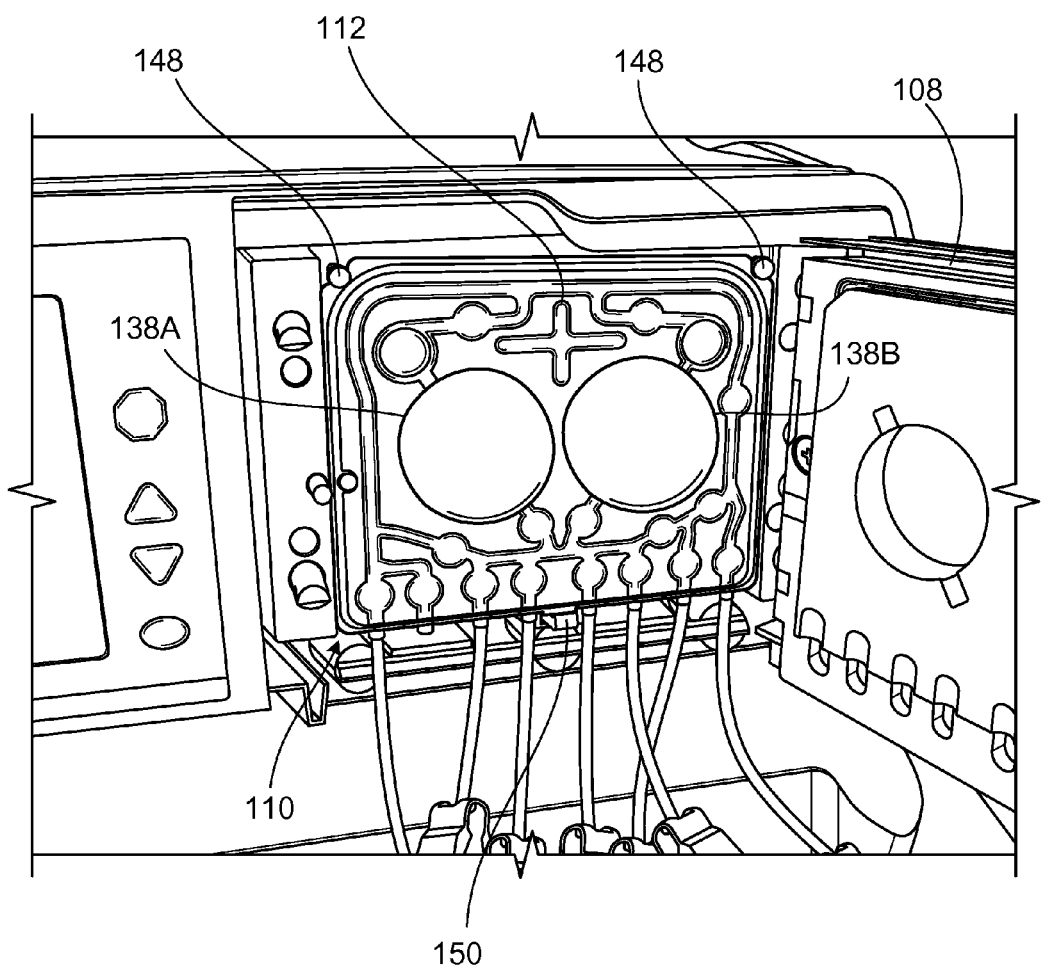
FIG. 9 is a partial perspective view of the PD cassette in the cassette compartment of the PD cycler of the PD system of FIG. 1.

As shown in FIG. 9, before treatment, the door 108 of the PD cycler 102 is opened to expose the cassette interface 110, and the cassette 112 is positioned with its membrane 140 adjacent to the cassette interface 110. While loading the cassette 112 into the PD cycler 102, the pistons 133A, 133B are typically retracted completely into the piston access ports 136A, 136B. This positioning of the pistons 133A, 133B can reduce the likelihood of damage to the pistons 133A, 133B during installation of the cassette 112. The cassette 112 is positioned such that the pump chambers 138A, 138B of the cassette 112 are aligned with the pistons 133A, 133B. In order to ensure that the pump chambers 138A, 138B align with the pistons 133A, 133B, the cassette 112 is positioned between the locating pins 148 and the tab 150 extending from the cassette interface 110. The asymmetrically positioned connectors 160 of the cassette act as keying features to reduce the likelihood that the cassette 112 will be installed with the membrane 140 facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward toward the door 108.

Figure 10A:
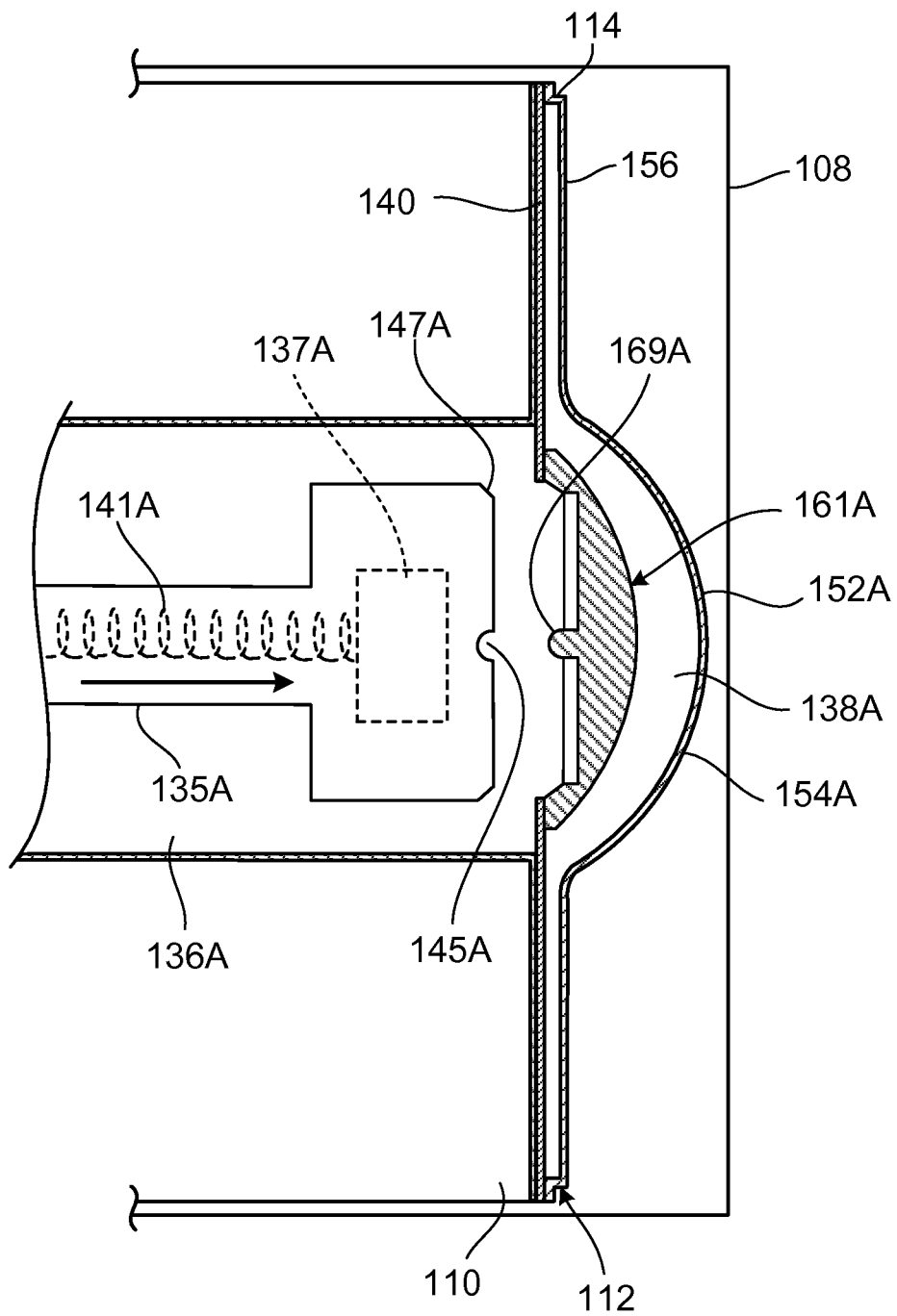
FIGS. 10A-10C are diagrammatic cross-sectional views of the PD cassette in the cassette compartment of the PD cycler of the PD system of FIG. 1, during different phases of operation.
Figure 10B:
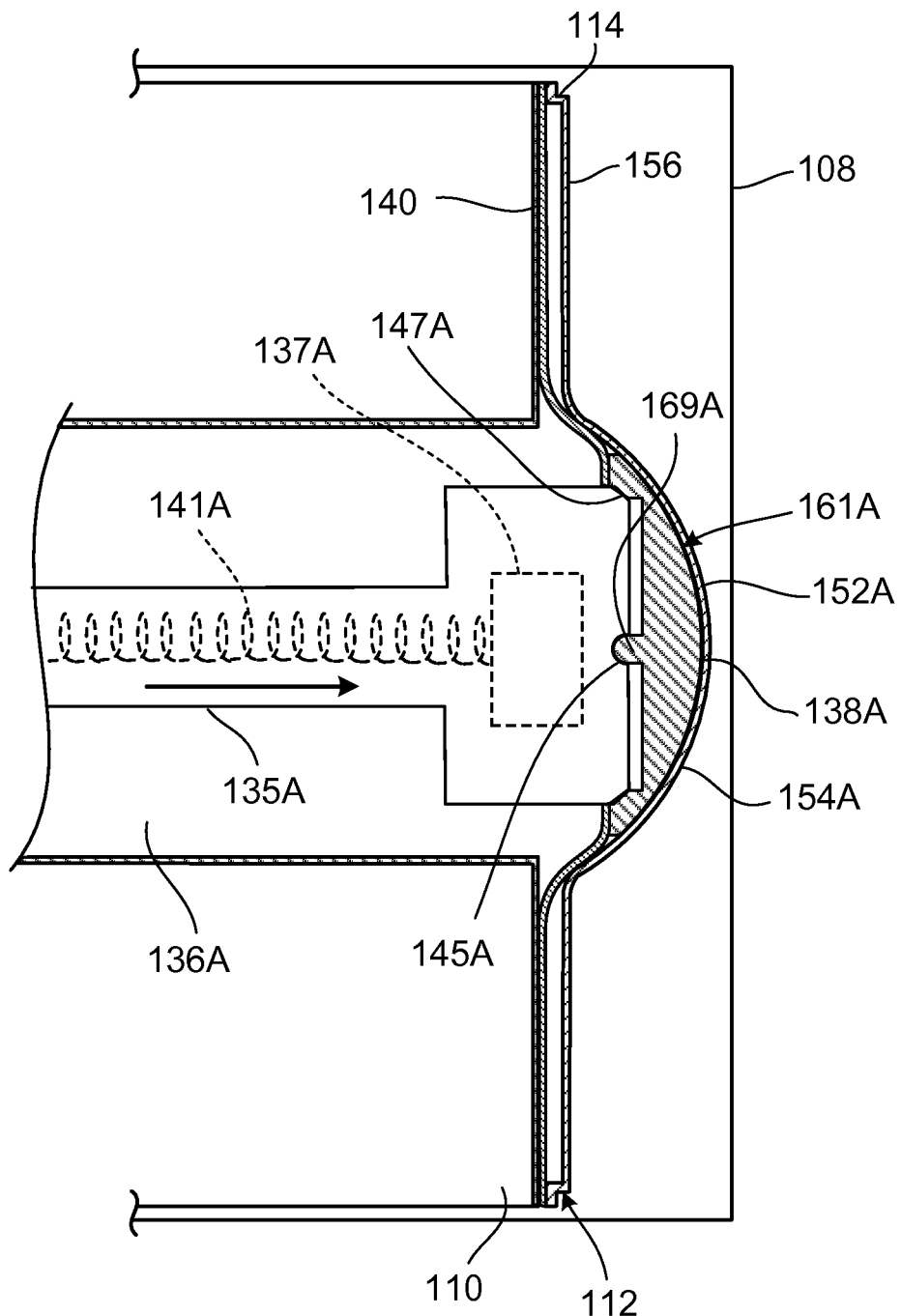
Figure 10C:
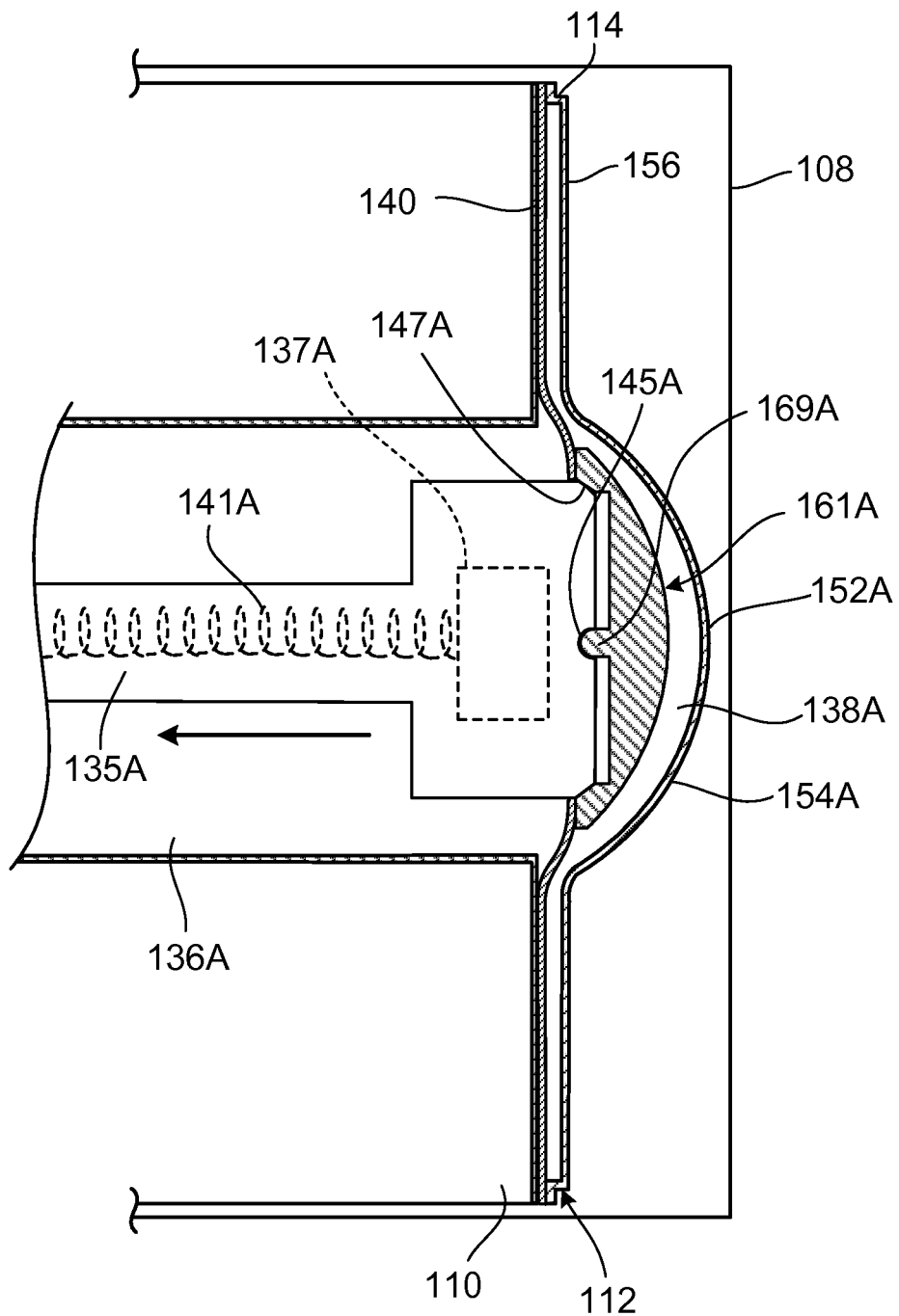

FIGS. 10A-10C illustrate the pump chamber 138A and its associated dome-shaped member 161A and piston 133A throughout different phases of operation. The other dome-shaped member 161B and piston 133B operate in a similar manner to pump dialysis solution to and from the other pump chamber 138B and thus, for simplicity, the operation of those components will not be separately described. Referring to FIG. 11A, with the cassette 112 positioned adjacent to the cassette interface 110, the door 108 is closed over the cassette 112 such that the cassette 112 is contained within the cassette compartment 114 between the door 108 and the cassette interface 110. An inflatable pad within the door 108 is then inflated to compress the cassette 112 between the door 108 and the cassette interface 110. This compression of the cassette 112 holds the projections 154A, 154B of the cassette 112 in the recesses 152A, 152B of the door 108 and presses the membrane 140 tightly against the raised ridges 165A, 165B, 167 extending from the planar surface of the rigid base 156 to form the enclosed fluid pathways 158, dome regions 146, and pump chambers 138A, 138B (shown in FIGS. 6 and 7).

As shown in FIG. 10B, after positioning the cassette 112 within the cassette compartment 114 and inflating the pad within the door 108, the piston 133A is advanced toward the cassette 112. As the piston 133A is advanced, a small amount of electrical power is delivered to the electromagnet 137A positioned within the piston head 134A. This creates a relatively weak magnetic field around the piston head 134A. As a result of this magnetic field, the piston 133A becomes coupled to the magnetically attractive dome-shaped member 161A as those components are brought into close proximity to one another. For example, a relatively low current can be applied to the electromagnet 137A by using a technique such as PWM described above. As the piston 133A is advanced toward the dome-shaped member 161A and the dome-shaped member 161A is drawn toward the piston 133A, the end portion of the piston head 134A enters the central cavity 168A of the dome-shaped member 161A. If the dome-shaped member 161A and the piston head 134A are slightly misaligned prior to this coupling process, the chamfered circumferential edge 147A of the piston 133A rides along the flange 164A of the dome-shaped member 161A and is urged into a centered position within the central cavity 168A as the piston 133A and the dome-shaped member 161A are moved toward one another. In addition, in the event that the dome-shaped member 161A and the piston 133A are slightly misaligned, the rounded leading end of the guiding peg 169A rides along the surface of the piston head 134A surrounding the guiding cavity 145A to center the dome-shaped member 161A over the piston 133A. As a result, the piston 133A and the dome-shaped member 161A become properly coupled by simply advancing the piston 133A while applying a low level of electrical power to the electromagnet 137A in the piston 133A.

After coupling the piston 133A to the dome-shaped member 161A in the manner described above, the piston 133A is further advanced to force the dome-shaped member 161A and the portion of the membrane 140 surrounding the dome-shaped member 161A toward the rigid base 156 of the cassette 112. As a result, the volume of the pump chamber 138A decreases, causing dialysis solution to be expelled from the pump chamber 138A via the fluid pathways 158 of the cassette 112 (shown in FIGS. 6-8).

After expelling the dialysis solution from the pump chamber 138A, the piston 133A is again retracted, as shown in FIG. 10C. The magnetic coupling of the dome-shaped member 161A causes the dome-shaped member 161A to move the membrane 140 in the same direction as the retracting piston 133A, thereby increasing the volume of the pump chamber 138A and generating vacuum pressure (e.g., a vacuum pressure of about 150 mbar to about 200 mbar) within the pump chamber 138A. As a result, dialysis solution is drawn into the pump chamber 138A of the cassette 112 via the fluid pathways 158 of the cassette 112 (shown in FIGS. 6-8).

After drawing the dialysis solution into the pump chamber 138A, the dialysis solution can then be forced out of the pump chamber 138A by again returning the piston 133A to the position shown in FIG. 10B, causing the membrane 140 and the dome-shaped member 161A to move toward the rigid base 156 and thus decreasing the volume of the pump chamber 138A.

In the event that the piston 133A becomes decoupled from the dome-shaped member 161A during the pumping process, the controller can attempt to recouple the piston 133A with the dome-shaped member 161A by applying current to the electromagnet 137A in the manner described above with respect to initially coupling the piston with the dome-shaped member. In some implementations, the controller can attempt to recouple the piston and dome-shaped member a specified number of times, e.g., five times or ten times, until either the piston and the dome-shaped member are detected as coupled, or the specified number of attempts has been reached. If the specified number of attempts has been reached, the controller can activate an alert notifying a user of the system 100 that a mechanical failure has occurred.

During operation, with the cassette 112 secured within the compartment 114, the pistons 133A, 133B are reciprocated to sequentially alter the volume of each of the pump chambers 138A, 138B. Typically, as the piston 133A is extended, the other piston head 134B is retracted, and vice versa. As a result, dialysis solution is expelled from the pump chamber 138A at the same time that dialysis solution is drawn into the pump chamber 138B, and vice versa. As noted above, while forcing dialysis solution into and out of the pump chambers 138A, 138B, certain inflatable members 142 of the PD cycler 102 can be selectively inflated to direct the pumped dialysis solution along desired pathways in the cassette 112.

Referring back to FIGS. 1 and 2, during PD treatment, the patient line 130 is connected to a patient's abdomen via a catheter, and the drain line 132 is connected to a drain or drain receptacle. The PD treatment typically begins by emptying the patient of spent dialysis solution that remains in the patient's abdomen from the previous treatment. To do this, the pump of the PD cycler 102 is activated to cause the pistons 133A, 133B to reciprocate and selected inflatable members 142 are inflated to cause the spent dialysis solution to be drawn into the pump chambers 138A, 138B of the cassette 112 from the patient and then pumped from the pump chambers 138A, 138B to the drain via the drain line 132.

After draining the spent dialysis solution from the patient, heated dialysis solution is transferred from the heater bag 124 to the patient. To do this, the pump of the PD cycler 102 is activated to cause the pistons 133A, 133B to reciprocate and certain inflatable members 142 of the PD cycler 102 are inflated to cause the heated dialysis solution to be drawn into the pump chambers 138A, 138B of the cassette 112 from the heater bag 124 via the heater bag line 128 and then pumped from the pump chambers 138A, 138B to the patient via the patient line 130.

Once the dialysis solution has been pumped from the heater bag 124 to the patient, the dialysis solution is allowed to dwell within the patient for a period of time. During this dwell period, toxins cross the peritoneum into the dialysis solution from the patient's blood. As the dialysis solution dwells within the patient, the PD cycler 102 prepares fresh dialysate for delivery to the patient in a subsequent cycle. In particular, the PD cycler 102 pumps fresh dialysis solution from one of the four full dialysis solution bags 122 into the heater bag 124 for heating. To do this, the piston motors of the PD cycler 102 are activated to cause the pistons 133A, 133B to reciprocate and certain inflatable members 142 of the PD cycler 102 are inflated to cause the dialysis solution to be drawn into the pump chambers 138A, 138B of the cassette 112 from the selected dialysis solution bag 122 via its associated line 126 and then pumped from the pump chambers 138A, 138B to the heater bag 124 via the heater bag line 128.

After the dialysis solution has dwelled within the patient for the desired period of time, the spent dialysis solution is pumped from the patient to the drain. The heated dialysis solution is then pumped from the heater bag 124 to the patient where it dwells for a desired period of time. These steps are repeated with the dialysis solution from two of the three remaining dialysis solution bags 122. The dialysis solution from the last dialysis solution bag 122 is typically delivered to the patient and left in the patient until the subsequent PD treatment.

While the dialysis solution has been described as being pumped into the heater bag 124 from a single dialysis solution bag 122, dialysis solution can alternatively be pumped into the heater bag 124 from multiple dialysis solution bags 122. Such a technique may be advantageous, for example, where the dialysis solutions in the bags 122 have different concentrations and a desired concentration for treatment is intermediate to the concentrations of the dialysis solution in two or more of the bags 122.

After completion of the PD treatment, the delivery of electrical power to the electromagnets 137A, 137B is stopped and the pistons 133A, 133B are retracted away from the cassette 112 to decouple the pistons 133A, 133B from the dome-shaped members 161A, 161B of the cassette 112. The door 108 of the PD cycler 102 is then opened and the cassette 112 is removed from the cassette compartment 114 and discarded.

Because the PD system 100 does not require a vacuum system to move the portions of the membrane 140 overlying the pump chambers 138A, 138B, a substantially airtight seal between the door 108 and the cassette interface 110 is typically not required. Thus, as compared to systems including a vacuum system adapted to retract portions of the cassette membrane overlying pump chambers, the door sealing mechanism of the PD cycler 102 can be simpler and more cost effective.

While certain implementations have been described, other implementations are possible.

Figure 11:
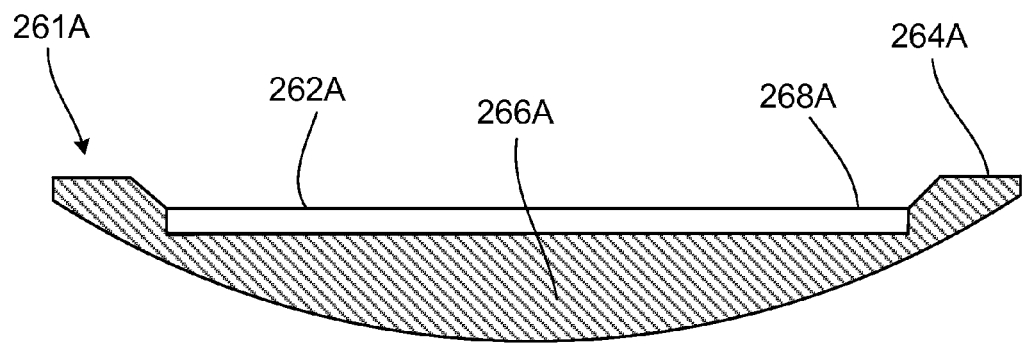
FIG. 11 is a cross-sectional view of a magnetically attractive dome-shaped member that includes no guiding peg.

While the magnetically attractive dome-shaped members have been described as including guiding pegs, in some implementations, the magnetically attractive dome-shaped members include no such guiding peg. As shown in FIG. 11, for example, a magnetically attractive dome-shaped member 261A includes a steel disk or plate 262A that sits within a central cavity 268A of the dome-shaped member 261A and is attached (e.g., thermally bonded) to a flat upper surface of a dome-shaped body 266A of the member 261A. While the dome-shaped member 261A includes no central guiding peg to facilitate alignment of the dome-shaped member with a piston, the inner circumferential surface of a flange 264A that extends upwardly from the body 266A is chamfered to facilitate such an alignment. Alternatively or additionally, the piston to be mated with the dome-shaped member 261A can include a chamfered circumferential leading edge to facilitate proper alignment of the piston with the dome-shaped member 261A as those components are coupled to one another.

While the steel disks of the above-described dome-shaped members 161A, 261A have been described as being thermally bonded to the dome-shaped bodies of those members, other techniques can alternatively or additionally be used to secure the steel disks to the dome-shaped bodies. In some implementations, for example, the steel disks are adhesively bonded to the dome-shaped bodies.

Figure 12:
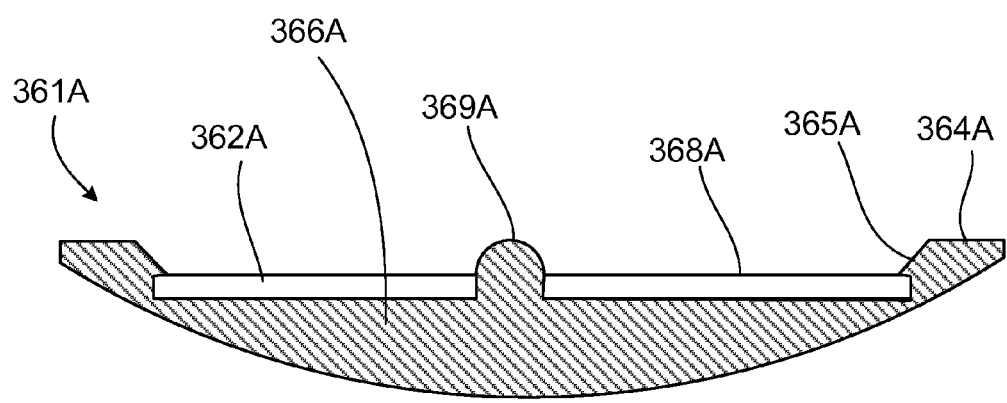
FIG. 12 is a cross-sectional view of a magnetically attractive dome-shaped member that includes a magnetically attractive disk that is secured to a body of the dome-shaped member by an interference fit or snap fit.

In certain implementations, the steel disks are mechanically secured to the dome-shaped bodies. As shown in FIG. 12, for example, a magnetically attractive dome-shaped member 361A includes a steel disk 362A that sits within a central cavity 368A of the dome-shaped member 361A and is secured to a flat upper surface of a dome-shaped body 366A of the member 361A by an interference fit. An annular flange 364A that extends from the body 366A includes an inner circumferential lip 365A that overhangs the steel disk 362A to retain the disk 362A within the cavity 368A. The lip 365A is sufficiently resilient that the disk 362A can be snapped into place within the cavity 368A during manufacturing. The dome-shaped member 361A includes a central guiding peg 369A and the inner circumferential surface of a flange 364A that extends upwardly from the body 366A is chamfered to facilitate alignment of the dome-shaped member 361A with a piston. However, it should be understood that the dome-shaped member could be formed without such alignment features. In some implementations, for example, the piston will include a chamfered leading circumferential edge that sufficiently aligns the piston with the dome-shaped member.

In some implementations, the steel disk of the dome-shaped member includes a central threaded bore that can matingly engage threads formed along the outer surface of the guiding peg of the dome-shaped member to secure the disk to the dome-shaped member. As a result of this securement technique, the steel disk can be removed from the dome-shaped member by unscrewing it from the guiding peg and can be replaced with a different disk if desired.

While the dome-shaped members of the above-described cassettes sit within an aperture of the cassette membrane and have a perimeter region or flange that is bonded to a portion of the membrane surrounding the apertures, other arrangements are possible. In some implementations, for example, the cassette membrane covers the pump chambers and underlies the domed sides (i.e., the sides that face the base of the cassette) of the dome-shaped members. The cassette membrane can, for example, be formed to include recessed regions that are sized and shaped to mate with the dome-shaped members. The peripheral edges of each dome-shaped member can be attached to the membrane, or the entire recessed regions of the membrane can be attached to the mated dome-shaped members.

Alternatively, the cassette membrane can be flat or planar and can overlie the flatter sides (i.e., the sides that face the pistons) of the dome-shaped members. The peripheral edges of each dome-shaped member can be attached to the membrane, or the entire portions of the membrane overlying the dome-shaped members can be attached to the dome-shaped members. The cassette membrane can stretch slightly towards the metal disks to allow the pistons to be coupled to the dome-shaped members. Alternatively, the cassette membrane can include subtle depressions that mate with the cavities of the dome-shaped members that receive the piston heads during use in order to reduce or minimize the amount of stretching induced in the membrane when the pistons are coupled to the dome-shaped members.

While the magnetically attractive disks of the dome-shaped members of the above-described cassettes have been described as being formed of steel, other constructions can be used. In certain implementations, for example, the magnetically attractive disk is coated with a biocompatible material, such as polytetrafluoroehtylene (PTFE), gold, or Parylene. After being coated with the biocompatible material, the magnetically attractive disk can be secured to the body of the dome-shaped member using any of the various securement techniques described for securing the disks to the bodies of the dome-shaped members.

Similarly, while the dome-shaped members have been described as including magnetically attractive plates in the form of disks, magnetically attractive plates of any of various other shapes can alternatively or additionally be used.

While the dome-shaped members have been described as including magnetically attractive plates, in certain implementations, the dome-shaped members include no such plates. In such implementations, for example, the bodies of the dome-shaped members can include a magnetically attractive material. The bodies of the dome-shaped members can, for example, be formed of any of the various magnetically attractive materials described herein with respect to the magnetically attractive disks or plates. In certain implementations, a magnetically attractive material is incorporated into the body of the dome-shaped member. For example, iron particles can be suspended within a polymeric body of the dome-shaped member.

While the pump chambers 138A, 138B of the cassette 112 have been described as being sized to pump about 12-13 ml of fluid with each piston stroke, it should be understood that any of the various cassettes described herein can include the pump chambers and associated dome-shaped members that are sized to pump different volumes of fluid. In certain implementations, for example, the pump chambers are sized to pump about 25-30 ml of fluid per piston stroke.

While the magnetically attractive members and the pump chambers of the above-described cassettes have been described as being dome-shaped, magnetically attractive members and pump chambers of other mating shapes can be used. For example, the magnetically attractive members and pump chambers can be cylindrical, rectangular, etc.

While the piston head 134A has been described as being formed of two separately molded halves that are bonded together, any of various other manufacturing methods that allow the electromagnet 137A to be positioned within the piston head 134A can be used.

While each of the piston heads 134A, 134B has been described as including a single electromagnet, it should be understood that multiple electromagnets can be contained within the piston heads to achieve a desired magnetic force.

In certain implementations, the pistons 133A, 133B can be easily disassembled and re-assembled. In such implementations, the electromagnets can be changed when it is desired to change the amount of magnetic force to be applied to the magnetically attractive dome-shaped member 161A. This can help to ensure that an optimal magnetic force is achieved between the pistons 133A, 133B and the dome-shaped members 161A, 161B for different types of treatments.

Other techniques can be used for detecting that the piston is coupled to the magnetically attractive dome-shaped member of the cassette or decoupled from the magnetically attractive dome-shaped member of the cassette. In some implementations, the electromagnet 137A has a second wire winding used only for detecting a change in voltage. For example, the second wire winding could have a relatively high resistance, such that the current across the second wire winding is relatively low (e.g., 10 mA or lower). The voltage across the second wire winding can be measured to determine if the piston is coupled or decoupled. The second wire winding could have physical characteristics that make it more sensitive to changes in inductance across the electrical circuit containing the second wire winding. For example, the second wire winding could be coiled in a manner differently than the first wire winding (e.g., coiled with tighter coils).

In some implementations, a secondary signal is applied to the wire winding (or, if used, the second wire winding), and the changes in the secondary signal are measured to determine if the piston is coupled to the magnetically attractive dome-shaped member of the cassette or decoupled from the magnetically attractive dome-shaped member of the cassette. For example, the secondary signal could be an oscillating signal such as a high-frequency signal. The amplitude of the signal may be greater than the voltage applied to the electromagnet 137A. For example, if the voltage applied to the electromagnet 137A is 24V, the amplitude of the secondary signal may be 50V or 100V. A change in voltage in the secondary signal may be more readily detected because the voltage of the secondary signal will be affected more greatly by the presence or absence of the magnetically attractive dome-shaped member. For example, the change in voltage may be proportional to the peak amplitude (e.g., 50V or 100V) of the secondary signal. If the secondary signal reaches its peak amplitude relatively infrequently, then the secondary signal will not significantly affect the voltage applied to the electromagnet 137A.

In some implementations, quantities other than voltage can be measured. As one example, a current sensor could be used to measure current across the wire winding of the electromagnet 137A. The voltage will have a deterministic relationship to the measured current. For example, the voltage across the wire winding can then be calculated based on the measured current and based on the resistance of the wire winding, which is typically a known quantity that is measured or calculated based on physical characteristics of the wire winding. Once the voltage is calculated (e.g., by the controller), the techniques for determining whether the piston is coupled or decoupled based on measured voltage can be applied to the calculated voltage.

In some implementations, frequency of a periodic signal is measured to determine whether the piston is coupled to or decoupled from the magnetically attractive dome-shaped member. The frequency of the signal as measured across the wire winding (or a second wire winding, if used) may indicate whether the piston is coupled or decoupled. In some examples, the signal could be the secondary signal described above, or the signal could be a PWM signal applied to the wire winding to power the electromagnet 137A, or the signal could be a different periodic signal than these. When the periodic signal is applied to the wire winding, the frequency of the signal as measured across the wire winding may be affected by the state of the dome-shaped member, e.g., whether the dome-shaped member is coupled to the piston. For example, when the piston contacts the dome-shaped member, the inductance of the electrical circuit that includes the wire winding may change. The frequency of the signal as measured across the wire winding may change in response, e.g., if the inductance increases, then the frequency of the signal increases. The controller can measure the frequency of the signal to determine if the piston is coupled to the dome-shaped member. In some implementations, if the controller is a microcontroller or other digital device, the wire winding can be connected to a circuit that includes an analog to digital converter (ADC), and the microcontroller can determine the frequency of the signal based on the digital signal output of the ADC.

While the pistons of the PD cyclers described above include electromagnets, permanent magnets can alternatively or additionally be used in certain cases. In such implementations, the magnetic coupling between the pistons and the dome-shaped members of the cassette can be broken by retracting the pistons a sufficient distance and with sufficient force to cause the pistons to become decoupled from the dome-shaped members.

While the magnets 135 have been described as being contained in the pistons of the PD cycler and the dome-shaped members of the cassettes have been described as including magnetically attractive materials that can be attracted to the magnets in the pistons, in some implementations, the dome-shaped members of the cassette contain the magnets and the pistons include the magnetically attractive materials that can be attracted to the magnets. In still other implementations, both the dome-shaped members of the cassette and the pistons of the PD cycler contain magnets.

While the dialysis systems described above include magnetic pistons that are coupled during use to magnetically attractive members of a cassette, in certain implementations, a dialysis system includes a dialysis machine having magnetic pistons that are magnetically coupled directly to a magnetically attractive membrane that partially forms the pump chambers of the cassette. The magnetic pistons can have the same general structure as the pistons described above. The magnetically attractive membrane is typically formed of the same materials as the membrane 140 described above but also includes an outer layer of magnetically attractive material. The outer layer can, for example, be a layer of magnetically attractive paint. The outer layer is typically restricted only to those portions of the membrane overlying the fluid pump chambers. However, the outer layer of magnetically attractive material can alternatively be applied to the entire surface of the membrane. One example of a suitable magnetically attractive paint is RUST-OLEUM® Specialty magnetic latex primer, available from RUST-OLEUM® Corporation (Vernon Hills, Ill.).

While the magnetically attractive membrane has been described as including an outer layer of magnetically attractive material, such as paint or primer, in certain implementations, the magnetically attractive material is incorporated into the body of the membrane. For example, iron particles can be suspended within the body of the membrane. As an alternative to or addition to iron particles, larger spheres of magnetic material can be encapsulated or bonded to the membrane.

While the membranes have been described as being attached to the cassette base only in the periphery edge region of the cassette base, in certain implementations the membranes are also attached (e.g., thermally or adhesively bonded) to the raised features extending from the planar surface of the base.

While the membranes have been described as covering substantially the entire surface of the base of the cassettes, membranes covering only the pump chambers or only a portion of the pump chambers can alternatively be used. In such implementations, for example, the fluid pathways extending from the pump chambers of the cassette can be provided by tubing that is fluidly connected to the pump chambers.

While the cassettes discussed above have been described as having two pump chambers, the cassettes can alternatively have more or fewer than two pump chambers.

While each of the pump chambers of the cassettes described above has been described as including a fluid inlet port and a fluid outlet port, the pump chambers can alternatively include a single port that is used as both an inlet and an outlet.

While certain cassettes have been described as being positioned between locating pins and a tab extending from a cassette interface of the PD cycler in order to hold the cassette in a position such that the piston heads align with the pump chambers of the cassette, other techniques for ensuring that the piston heads align with the pump chambers can alternatively or additionally be used. In some implementations, for example, the cassette is placed against the door of the PD cycler with the hollow projections of the cassette disposed in recesses of the PD cycler's door. The cassette is held in this position by retainer clips attached to the door. Upon closing the door, the piston heads of the PD cycler align with the pump chambers of the cassette.

While certain PD cyclers above have been described as including a touch screen and associated buttons, the PD cycler can include other types of screens and user data entry systems. In certain implementations, for example, the cycler includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the doors of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation.

While the PD cyclers discussed above include inflatable pads in their doors to compress the cassette between the door and the cassette interface, the PD cyclers can alternatively or additionally include inflatable pads positioned behind the cassette interface. Similarly, as an alternative to or in addition to using an inflatable pad to compress the cassette, other mechanisms suitable for compressing the cassette can be used.

While the cassettes described above have been described as being part of a PD system, these types of cassettes can be used in any of various other types of cassette-based medical fluid pumping systems. Other examples of medical fluid pumping systems with which cassettes described herein can be used include hemodialysis systems, blood perfusion systems, and intravenous infusion systems.

Similarly, while the cassettes have been described as being used to pump dialysis solution, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

What is claimed is:

1. A medical fluid pumping system, comprising:
   a medical fluid cassette defining a fluid pump chamber;
   a medical fluid pumping machine defining a cassette compartment and comprising an electromagnetic piston that aligns with the fluid pump chamber of the medical fluid cassette when the medical fluid cassette is disposed in the cassette compartment, the electromagnetic piston comprising an electromagnet connected to a wire winding, the electromagnet being configured to receive electrical power through the wire winding to magnetize the electromagnet, wherein the electromagnetic piston is configured to be coupled to the medical fluid cassette when the electromagnet is magnetized and to be decoupled from the medical fluid cassette when the electromagnet is not magnetized, wherein the medical fluid cassette is configured to be removed from the cassette compartment;
   a sensor electrically connected to the wire winding of the electromagnetic piston, the sensor being configured to detect an electrical characteristic across the wire winding and to generate an electrical signal indicative of the detected electrical characteristic, the electric characteristic being indicative of coupling between the electromagnetic piston and the medical fluid cassette, wherein the electromagnetic piston is configured to be coupled to and decoupled from the medical fluid cassette; and
   a controller configured to receive the electrical signal from the sensor connected to the wire winding, and adjust the electrical power delivered through the wire winding to the electromagnetic piston based on determining whether the electrical signal indicates that the electromagnetic piston and the medical fluid cassette are coupled.

2. The medical fluid pumping system of claim 1, wherein the electrical characteristic is selected from the group consisting of voltage, current, and frequency.

3. The medical fluid pumping system of claim 1, wherein the controller is configured to:
   apply the power to the electromagnetic piston to couple the electromagnetic piston to the medical fluid cassette, and
   receive the electrical signal and adjust the applied power based on the electrical characteristic detected by the sensor, the electrical characteristic being a component of the applied power.

4. The medical fluid pumping system of claim 1, wherein the electrical characteristic is associated with the electrical power to magnetize the electromagnet.

5. The medical fluid pumping system of claim 1, wherein the electrical characteristic is sensitive to a change in inductance across the wire winding.

6. The medical fluid pumping system of claim 1, wherein the controller is configured to detect a spike in the electrical characteristic when the electromagnetic piston is coupled to the medical fluid cassette.

7. The medical fluid pumping system of claim 1, wherein the controller is configured to determine whether the electrical characteristic indicates that the electromagnetic piston and the medical fluid cassette are coupled based on first and second values on a look-up table, the first value corresponding to an average value of the electrical characteristic when the electromagnetic piston is coupled to the medical fluid cassette, and the second value corresponding to an average value of the electrical characteristic when the electromagnetic piston is decoupled from the medical fluid cassette.

8. A medical fluid pumping machine, comprising:
   an electromagnetic piston, the electromagnetic piston comprising an electromagnet connected to a wire winding, the electromagnet being configured to receive electrical power through the wire winding to magnetize the electromagnet, wherein the electromagnetic piston is configured to be coupled to a medical fluid cassette when the electromagnet is magnetized and to be decoupled from the medical fluid cassette when the electromagnet is not magnetized;
   a sensor electrically connected to the wire winding of the electromagnetic piston, the sensor being configured to detect an electrical characteristic across the wire winding and to generate an electrical signal indicative of the detected electrical characteristic, the electric characteristic being indicative of coupling between the electromagnetic piston and the medical fluid cassette, wherein the electromagnetic piston is configured to be coupled to and decoupled from the medical fluid cassette; and a controller configured to receive the electrical signal from the sensor connected to the wire winding, and adjust the electrical power delivered through the wire winding to the electromagnetic piston based on determining whether the electrical signal indicates that the electromagnetic piston and the medical fluid cassette are coupled.

9. The medical fluid pumping machine of claim 8, wherein the electrical characteristic is selected from the group consisting of voltage, current, and frequency.

10. The medical fluid pumping machine of claim 8, wherein the controller is configured to:
apply the power to the electromagnetic piston to couple the electromagnetic piston to the medical fluid cassette,
receive the electrical signal and adjust the applied power based on the electrical characteristic detected by the sensor, the electric characteristic being a component of the applied power.

11. The medical fluid pumping machine of claim 8, wherein the electrical characteristic is associated with the electrical power to magnetize the electromagnet.

12. The medical fluid pumping machine of claim 8, wherein the electrical characteristic is sensitive to a change in inductance across the wire winding.

13. The medical fluid pumping machine of claim 8, wherein the controller is configured to detect a spike in the electrical characteristic when the electromagnetic piston is coupled to the medical fluid cassette.

14. The medical fluid pumping machine of claim 8, wherein the controller is configured to determine whether the electrical characteristic indicates that the electromagnetic piston and the medical fluid cassette are coupled based on first and second values on a look-up table, the first value corresponding to an average value of the electrical characteristic when the electromagnetic piston is coupled to the medical fluid cassette, and the second value corresponding to an average value of the electrical characteristic when the electromagnetic piston is decoupled from the medical fluid cassette.

15. A method comprising:
supplying electrical power through a wire winding to an electromagnet of a piston to magnetize the electromagnet;
receiving an electrical signal indicative of an electrical characteristic across the wire winding;
determining whether the piston is coupled to a magnetically attractive member of a medical fluid cassette based on the electrical characteristic of across the wire winding, wherein the piston is configured to be coupled to and decoupled from the magnetically attractive member; and
adjusting the electrical power delivered through the wire winding based on determining whether the piston is coupled to the magnetically attractive member of the medical fluid cassette.

16. The method of claim 15, wherein the electrical characteristic is measured across the wire winding of the electromagnet.

17. The method of claim 15, wherein the electrical characteristic is selected from the group consisting of voltage, current, and frequency.

18. The method of claim 15, wherein the electrical characteristic is a component of the supplied electrical power.

19. The method of claim 15, wherein the electrical characteristic is associated with the electrical power to magnetize the electromagnet.

20. The method of claim 15, wherein the electrical characteristic is sensitive to a change in inductance across the wire winding.

21. The method of claim 15, wherein determining whether the piston is coupled to the magnetically attractive member of the medical fluid cassette comprises determining whether the piston is coupled to the magnetically attractive member of the medical fluid cassette based on detecting a spike in the electrical characteristic.

22. The method of claim 15, wherein determining whether the electrical characteristic indicates that the piston and the medical fluid cassette are coupled based on first and second values on a look-up table, the first value corresponding to an average value of the electrical characteristic when the piston is coupled to the medical fluid cassette, and the second value corresponding to an average value of the electrical characteristic when the piston is decoupled from the medical fluid cassette.

* * * * *